US012806162B2

(12) United States Patent
Altier

(10) Patent No.: US 12,806,162 B2
(45) Date of Patent: Nov. 24, 2026

(54) **LONG CHAIN FATTY ACID FORMULATIONS AND THEIR USE IN INHIBITING *SALMONELLA* INFECTION**

(71) Applicant: CORNELL UNIVERSITY, Ithaca, NY (US)

(72) Inventor: Craig Altier, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 480 days.

(21) Appl. No.: 16/854,969

(22) Filed: Apr. 22, 2020

(65) Prior Publication Data

US 2020/0330420 A1 Oct. 22, 2020

Related U.S. Application Data

(60) Provisional application No. 62/836,901, filed on Apr. 22, 2019.

(51) Int. Cl.

| | |
|---|---|
| ***A01N 43/00*** | (2006.01) |
| ***A01N 43/46*** | (2006.01) |
| ***A23K 20/105*** | (2016.01) |
| ***A23K 20/158*** | (2016.01) |
| ***A61K 9/48*** | (2006.01) |
| ***A61K 31/201*** | (2006.01) |
| ***A61K 31/55*** | (2006.01) |
| ***A61K 47/10*** | (2017.01) |
| ***A61K 47/20*** | (2006.01) |
| ***A61K 47/44*** | (2017.01) |
| *A61K 9/00* | (2006.01) |

(52) U.S. Cl.

CPC .......... *A61K 31/201* (2013.01); *A23K 20/105* (2016.05); *A23K 20/158* (2016.05); *A61K 9/48* (2013.01); *A61K 47/10* (2013.01); *A61K 47/20* (2013.01); *A61K 47/44* (2013.01); *A61K 9/0053* (2013.01)

(58) Field of Classification Search

CPC .................................................... A61K 31/575

See application file for complete search history.

(56) References Cited

U.S. PATENT DOCUMENTS

| | | | | |
|---|---|---|---|---|
| 4,472,432 | A | 9/1984 | Iwamura et al. | |
| 6,051,754 | A | 4/2000 | Knutzon | |
| 6,075,183 | A | 6/2000 | Knutzon et al. | |
| 6,432,415 | B1 | 8/2002 | Osborne et al. | |
| 7,807,849 | B2 | 10/2010 | Singh et al. | |
| 2013/0131172 | A1* | 5/2013 | Zhang .................. | A61K 31/201 554/230 |

FOREIGN PATENT DOCUMENTS

| | | | | |
|---|---|---|---|---|
| WO | 2009/117130 A2 | 9/2009 | | |
| WO | WO-2014134701 A1 * | 9/2014 | ............. | A61P 31/04 |

OTHER PUBLICATIONS

Barber, C.E., "A novel regulatory system required for pathogenicity of Xanthomonas campestris is mediated by a small diffusible signal molecule", Molecular Microbiology (1997), pp. 555-566, 24(3).

Boon, C., et al., "A novel DSF-like signal from Burkholderia cenocepacia interferes with Candida albicans morphological transition", The ISME Journal (2008), pp. 27-36, 2.

Datsenko, K.A., et al., "One-step inactivation of chromosomal genes in *Escherichia coli* K-12 using PCR products", PNAS, Jun. 6, 2000, pp. 6640-6645, vol. 97, No. 12.

Dow, J.M., "Diffusible signal factor-dependent quorum sensing in pathogenic bacteria and its exploitation for disease control", Journal of Applied Microbiology 2016, pp. 2-11, 122.

Gantois, I., et al., "Butyrate Specifically Down-Regulates *Salmonella* Pathogenicity Island 1 Gene Expression", Applied and Environmental Microbiology, Jan. 2006, pp. 946-949, vol. 72, No. 1.

Golubeva, Y.A., et al., "Intestinal Long-Chain Fatty Acids Act as a Direct Signal To Modulate Expression of the *Salmonella* Pathogenicity Island 1 Type III Secretion System", mBio, Jan./Feb. 2016, pp. 1-9, vol. 7, Issue 1.

Hung, C.-C., et al., "The intestinal fatty acid propionate inhibits *Salmonella* invasion through the post-translational control of HilD", Molecular Microbiology (2013), pp. 1045-1060, 87(5).

Ionescu, M., et al., "Promiscuous Diffusible Signal Factor Production and Responsiveness of the Xylella fastidiosa Rpf System", Jul./Aug. 2016, pp. 1-12, vol. 7, Issue 4.

(Continued)

*Primary Examiner* — Layla Soroush

(74) *Attorney, Agent, or Firm* — Scully, Scott, Murphy & Presser, P.C.

(57) ABSTRACT

A method for inhibiting or preventing *Salmonella* invasion of the intestinal epithelium in a subject, the method comprising enterally administering to the subject a pharmaceutically effective amount of a fatty acid dissolved or suspended in a pharmaceutically acceptable carrier, wherein the fatty acid contains 10 to 30 carbon atoms, wherein the fatty acid is more particularly an unsaturated fatty acid containing 1-4 carbon-carbon double bonds and/or 1 or 2 carbon-carbon triple bonds, or the fatty acid is more particularly a cis-unsaturated fatty acid, or the fatty acid is more particularly a cis-2-unsaturated fatty acid having the formula:

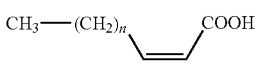

(1)

wherein n is an integer of 6-26, and the fatty acid optionally includes a second carbon-carbon double bond resulting from removal of two hydrogen atoms on adjacent carbon atoms.

10 Claims, 18 Drawing Sheets

(56) References Cited

OTHER PUBLICATIONS

Richardson, M.B., et al., "A practical synthesis of long-chain iso-fatty acids (iso-C12-C19) and related natural products", Beilstein Journal of Organic Chemistry 2013, pp. 1807-1812, 9.
Wang, L.-H., et al., "A bacterial cell-cell communication signal with cross-kingdom structural analogues", Molecular Microbiology (2004), pp. 903-912, 51(3).

* cited by examiner cis-2-Hexadecenoic acid cis-2-Eicosenoic acid

Oleic acid (6A)

(6B)

LONG CHAIN FATTY ACID FORMULATIONS AND THEIR USE IN INHIBITING *SALMONELLA* INFECTION

CROSS REFERENCE TO RELATED APPLICATION

This application claims the benefit of priority from U.S. Provisional Application No. 62/836,901, filed on Apr. 22, 2019.

GOVERNMENT SUPPORT

This invention was made with government support under Competitive Grant No. 2016-10255 awarded by the USDA Agriculture and Food Research Initiative and Grant No. 2014-67015-21697 awarded by NIH/USDA NIFA Dual Purpose with Dual Benefit Program. The government has certain rights in the invention.

FIELD OF THE INVENTION

The invention generally relates to treating, inhibiting, or preventing *Salmonella* infection. The invention more particularly relates to the use of long chain fatty acids in treating, inhibiting, or preventing *Salmonella* infection.

BACKGROUND OF THE INVENTION

Non-typhoidal *salmonellosis*, caused by serovars of *Salmonella enterica* subspecies *enterica*, remains a leading cause of death among foodborne bacterial diseases both domestically and globally. *Salmonella* also presents a significant health and economic problem to agriculture and humans. Its burden is further aggravated by its increasing resistance to conventional antibiotics. Thus, antibiotics, the typical response to bacterial infections, are seldom useful and risk the spread of resistance.

Epithelial cell invasion, encoded within the *Salmonella* Pathogenicity Island 1 (SPI1), has been shown to be essential for intestinal penetration and consequently disease carriage. Substantial efforts to inhibit *Salmonella* epithelial cell invasion have been made, but they have been largely unsuccessful. A non-antibiotic method for inhibiting *Salmonella* infection by corresponding inhibition of epithelial cell invasion would represent a significance advance in the effort to combat *Salmonella* infection.

SUMMARY OF THE INVENTION

In one aspect, the present disclosure is directed to compositions containing one or more long chain fatty acids dissolved or suspended in a pharmaceutically acceptable carrier or a feed formulation for humans or animals. The pharmaceutically acceptable carrier is typically a liquid, such as, for example, an alcohol, glycol, oil, paraffin, or polar aprotic solvent, such as dimethyl sulfoxide. As further discussed below, the pharmaceutical compositions have herein been found to inhibit *Salmonella* infection by corresponding inhibition of epithelial cell invasion by *Salmonella*.

The long chain fatty acid typically contains 10-30 carbon atoms. In some embodiments, the fatty acid is saturated, while in other embodiments the fatty acid is unsaturated. In some embodiments, the unsaturated fatty acid is more specifically a cis-unsaturated fatty acid, or more specifically, a cis-2-unsaturated fatty acid, such as depicted by the following formula:

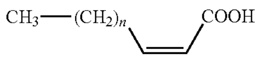

(1)

wherein n is an integer of 6-26, and the fatty acid optionally includes a second carbon-carbon double bond resulting from removal of two hydrogen atoms on adjacent carbon atoms. In specific embodiments, n may be 6, 7, 8, 9, 10, 11, 12, 13, 14, 15, 16, 18, 20, 22, 24, or 26, or within a range therein (e.g., 8-26, 8-20, 6-16, 7-16, or 8-16). A few particular unsaturated fatty acids having a cis-oriented double bond at the 2-position include (Z)-dec-2-enoic acid, (Z)-dodec-2-enoic acid, (Z)-hexadec-2-enoic acid, and (Z)-icos-2-enoic acid (common names cis-2-decenoic acid, cis-2-dodecenoic acid, cis-2-hexadecenoic acid, and cis-2-eicosenoic acid, respectively).

In another aspect, the present disclosure is directed to methods for treating (e.g., inhibiting or preventing) *Salmonella* infection by inhibiting or preventing *Salmonella* invasion of the intestinal epithelium in the subject. In the method, a pharmaceutically effective amount of the long chain fatty acid, typically in the form of a pharmaceutical preparation, as described above, is enterally administered to the subject. In some embodiments, the subject has already contracted *Salmonella* when the subject is administered the long chain fatty acid, in which case the method of treating functions to inhibit or prevent *Salmonella* invasion of the intestinal epithelium in the subject, thereby inhibiting or preventing infection of the subject by *Salmonella*. In other embodiments, the subject has not contracted *Salmonella* when the subject is administered the long chain fatty acid, in which case the method of treating functions as a preventative measure to inhibit or prevent *Salmonella* invasion of the intestinal epithelium in the subject, thereby preventing or inhibiting *Salmonella* infection, should the subject contract *Salmonella*.

In some embodiments, the one or more fatty acids are dissolved in an organic solvent suitable for oral administration to humans or animals (e.g., dimethyl sulfoxide or ethanol) and are provided ad lib in drinking water or other consumable liquid at sufficient concentrations (e.g., at least 500 nM or 1 μM to 2 mM) to inhibit or prevent *Salmonella* invasion of the intestinal epithelium. In other embodiments, the subject is administered the fatty acid by drinking a solution or suspension of the fatty acid or by swallowing the fatty acid, typically within a vehicle, such as within a capsule or microcapsule. The fatty acid is typically administered in a dosage of 50 mg to 2000 mg daily for at least one, two, three, or more days.

The present invention operates on the premise that *Salmonella* can be controlled not by trying to kill it, but instead by reducing its virulence. The specific virulence trait being targeted herein is essential to the success of this approach: invasion of the intestinal epithelium by *Salmonella* inflames the intestinal lumen, creating an environment that promotes the growth of *Salmonella* within the gut, while the invading bacteria themselves die. The implications of this lifecycle are paramount to the development of this novel means to prevent *Salmonella* infections. Resistance to any anti-*Salmonella* drug may occur, as it has for antimicrobials, through bacterial mutations. Targeting invasion as a means to control

*salmonellosis*, however, prevents the propagation of this resistance. Because invading bacteria are killed in the process, the small number of resistant mutants that arise may provide some brief, temporary advantage in infection, but will not proliferate to pass on their resistance trait. Thus, *Salmonella* is very unlikely to gain resistance to compounds described herein that inhibit invasion because resistant mutants are destined to die during the invasion process and so will not become fixed in the population. The present invention exploits this step in *Salmonella* pathogenesis by using long chain fatty acids (e.g., cis-2-unsaturated fatty acids) that specifically inhibit invasion, thereby providing a durable class of preventatives and therapeutics.

The present invention advantageously provides a non-antibiotic yet effective method for preventing *Salmonella* infection of the intestines in a subject. The subject may be human, or an animal, such as livestock or poultry. A particular advantage of the inventive method is the avoidance of resistance, as commonly encountered with antibiotics. The method involves enteral administration of a pharmaceutically effective amount of a long chain fatty acid, such as a cis-unsaturated fatty acid, or more particularly, a cis-2-unsaturated long chain fatty acid. The long chain fatty acid achieves this effect by inhibiting expression of at least one *Salmonella* invasion gene.

BRIEF DESCRIPTION OF THE FIGURES

FIG. 1A: Luminescence vs. time data showing that cis-2-hexadecenoic acid inhibits *Salmonella* hilA expression while its trans-isomer is less potent. A strain carrying a hilA::luxCDABE reporter plasmid was grown in the presence of 20 μM fatty acids. FIG. 1B: Luminescence vs. time data showing that cis-2-hexadecenoic acid potently represses hilA expression at low concentrations. FIG. 1C: Luminescence vs. time data showing that the DSF potently represses the *Salmonella* type III secretion complex effector protein gene sopB. A strain carrying a sopB::luxCDABE reporter plasmid was grown in the presence of 20 μM cis-2-hexadecenoic acid. FIG. 1D: Graph showing that the DSF reduces HEp-2 cell invasion by *Salmonella*. The number of bacteria that invaded HEp-2 cells in the presence of the DSF was determined using a gentamicin protection assay. FIG. 1E: Luminescence vs. time data showing that cis-2-hexadecenoic acid contains an effective chain length for repressing hilA. FIG. 1F: Structures of cis-2-hexadecenoic acid and the controls, cis-2-eicosenoic acid and oleic acid. Expression of lux reporter fusions is presented as luminescence normalized to bacterial culture density. Error bars represent standard deviations of 5 replicates for A, B, C and E and 4 for D. The control culture contained the vehicle only at identical concentration as the chemical-containing cultures. Asterisks denote expression levels significantly different from the control (**-P<0.0001, *-P<0.001).

FIG. 3A: The DSF represses hilA less potently in the absence of the long chain fatty acid transporter fadL. A ΔfadL mutant carrying a hilA::luxCDABE reporter plasmid was grown in the presence of 1 μM DSF. FIG. 3B: A ΔfadE mutant carrying a hilA::lux reporter fusion was grown in the presence of 20 μM cis-2-unsaturated fatty acids. Expression of hilA is presented as peak luminescence normalized to bacterial culture density. Error bars represent standard deviations of 5 replicates. The control culture contained the vehicle only at identical concentration as the chemical-containing cultures. Asterisks denote expression levels significantly different from the control (****-P<0.0001).

FIG. 4A: Luminescence vs. time data showing that loss of hilD reduces the repressive effects of cis-2-hexadecenoic acid on sopB. A ΔhilD mutant strain carrying a sopB::lux reporter fusion, and with rtsA under a tetracycline-inducible promoter was grown in the presence of 20 μM cis-2-hexadecenoic acid. FIG. 4B: Luminescence vs. time data showing that the DSF's repressive effects on sopB are independent of the HilD negative regulators HilE and Lon. Strains lacking hilE and Ion, and carrying a sopB::lux reporter fusion were grown in the presence of 20 μM cis-2-hexadecenoic acid. FIG. 4C: data showing that cis-2-unsaturated fatty acids repress hilD post-transcriptionally. A strain lacking rtsA and hilC, and with hilD under a tetracycline-inducible promoter was grown in the presence of 20 μM cis-2-unsaturated fatty acids. A tetracycline concentration inducing hilD to a level equivalent to the wild type was used. Expression of lux reporter fusions is reported as mean luminescence normalized to bacterial culture density. Error bars represent standard deviations of 5 replicates. The control culture contained the vehicle only (DMSO for cis-2-hexadecenoic acid and cis-2-eicosenoic acid, and ethanol for oleic acid) at identical concentration to the treated culture. Asterisks denote expression levels significantly different from the control (**-P<0.0001, -P<0.01).

FIG. 5A: Western blot data showing that cis-2-unsaturated fatty acids reduce HilD half-life in the presence of Lon. Strains carrying a hilD-3×FLAG construct under the control of a tetracycline-inducible promoter, with Lon present or absent, were grown in the presence of 20 μM cis-2-unsaturated fatty acids. HilD half-life was determined by western blotting for 3×FLAG. FIG. B: Luminescence vs. time data showing that cis-2-unsaturated fatty acids repress hilA expression in the absence of Lon. A strain carrying a hilA::lux reporter fusion with a Δlon mutation was grown in the presence of 20 μM of the fatty acids. Expression of hilA is presented as luminescence normalized to bacterial culture density. The control culture contained the vehicle only (DMSO for cis-2-hexadecenoic acid and cis-2-eicosenoic acid, and ethanol for oleic acid) at identical concentration to the treated culture.

FIG. 6A: Data showing that cis-2-fatty acids repress hilA in the presence of rtsA only. FIG. 6B: Data showing that cis-unsaturated fatty acids repress hilA in the presence of hilC only. Expression of the lux reporter fusion is presented as peak luminescence normalized to bacterial culture density. The control culture contained the vehicle only (DMSO for cis-2-hexadecenoic acid and cis-2-eicosenoic acid, and ethanol for oleic acid) at identical concentration to the treated culture. Asterisks denote expression levels significantly different from the control (*-P<0.001, -P<0.01).

DETAILED DESCRIPTION OF THE INVENTION

Figure 1A:
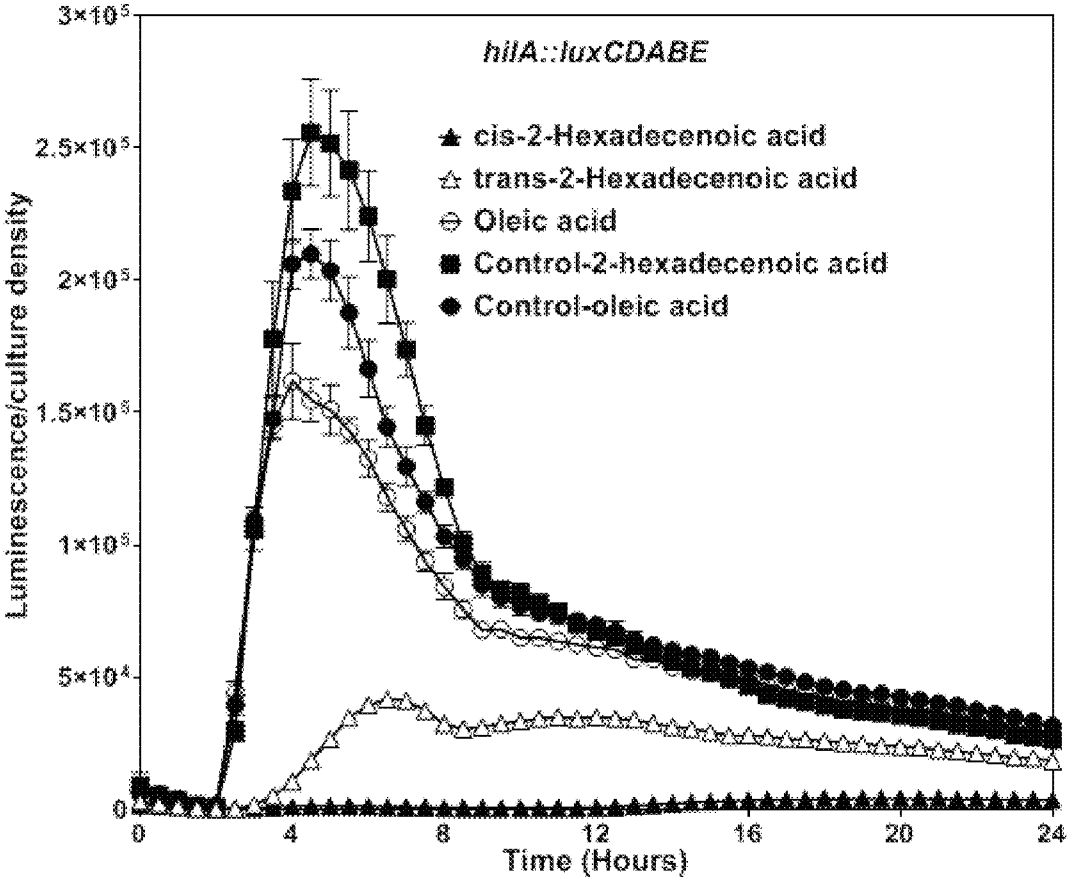
FIGS. 1A-1F. Cis-2-hexadecenoic (the selected DSF) acid potently represses virulence expression.

In one aspect, the invention is directed to compositions that contain a long chain fatty acid (also referred to herein as a "fatty acid") dissolved or suspended in a pharmaceutically acceptable carrier (also referred to herein as a vehicle or excipient) or a feed (enteric) formulation for humans or animals, wherein the fatty acid contains 10-30 carbon atoms. In different embodiments, the fatty acid contains 10, 12, 14, 16, 18, 20, 22, 24, 26, 28, or 30 carbon atoms, or a number of carbon atoms within a range bounded by any two of the foregoing values. The fatty acid may be saturated or unsaturated. In the case of unsaturated fatty acids, the fatty acid typically contains one, two, three, or four carbon-carbon double bonds. The fatty acid may instead or in addition contain one or two carbon-carbon triple bonds. The fatty acid may also be linear or branched. As used herein, the term "fatty acid" is intended to include salts of fatty acids, such as sodium, potassium, or magnesium salts, unless otherwise specified as the protonated form. The carbon of the carboxylic acid group is typically bound to a methylene ($CH_2$) group or unsaturated CH group. Notably, the term "fatty acid," as used herein, refers to "free" fatty acids, i.e., not fatty acid esters as found in triglycerides, diglycerides, or monoglycerides, also commonly known as fats or oils. Thus, a plant-based or animal-based oil that contains a glyceride form of a fatty acid does not itself constitute a fatty acid. Nevertheless, as further discussed below, the plant-based or animal-based oil may be used as a solvent in which one or more free fatty acids are incorporated. The pharmaceutical composition can be prepared by any of the methods well known in the art for producing solid-in-liquid or liquid-in-liquid solutions or suspensions. In some embodiments, a surfactant is included to aid dissolution of the fatty acid in the solvent.

In one set of embodiments, the fatty acid is saturated and may be linear or branched. Linear saturated fatty acids may be conveniently expressed by the formula $CH_3(CH_2)_rCOOH$, wherein r is a value of 8-28. In different embodiments, r may be, for example, 8, 10, 12, 14, 16, 18, 20, 22, 24, 26, or 28, or a value within a range bounded by any two of the foregoing values. Branched saturated fatty acids contain precisely or at least one, two, or three of the hydrogen atoms in methylene groups in the foregoing formula substituted by an equivalent number of methyl groups, provided that the total number of carbon atoms within the branched fatty acid remains within the range of 10-30.

Some examples of linear saturated fatty acids include capric acid (r=8), undecanoic acid (r=9), lauric acid (r=10), myristic acid (r=12), palmitic acid (r=14), stearic acid (r=16), arachidic acid (r=18), behenic acid (r=20), tricosylic acid (r=21), lignoceric acid (r=22), cerotic acid (r=24), montanic acid (r=26), and melissic acid (r=28). Some examples of branched saturated fatty acids include 3-methyl-decanoic acid, 9-methyldecanoic acid, 9-methyl-dodecanoic acid, 10-methyl-undecanoic acid (isolauric acid), 12-methyl-tridecanoic acid (isomyristic acid), 12-methyl-tetradecanoic acid (sarcinic acid), 13-methyl-tetradecanoic acid, 14-methyl-pentadecanoic acid (isopalmitic acid), 16-methyl-heptadecanoic acid (isostearic acid), 18-methyl-nonadecanoic acid (isoarachidic acid), 2,6-dimethyl-nonadecanoic acid, 2,6-dimethylundecanoic acid, 2,6-dimethyldodecanoic acid, 4,12-dimethyltridecanoic acid, 2,6-dimethylhexadecanoic acid, and 3,13,19-trimethyl-tricosanoic acid.

In another set of embodiments, the fatty acid is unsaturated by containing one, two, three, or four carbon-carbon double bonds and/or one or two carbon-carbon triple bonds. The unsaturated fatty acid may be linear or branched. Moreover, one or more carbon-carbon double bonds in the fatty acid may be cis (Z) or trans (E). Linear unsaturated fatty acids may be conveniently expressed by the above formula $CH_3(CH_2)_rCOOH$, except provided that at least two hydrogen atoms on adjacent carbon atoms are replaced with a double bond between the adjacent carbon atoms, wherein r is a value of 8-28 or any of the exemplary specific values or ranges therein, as provided above. Branched unsaturated fatty acids contain precisely or at least one, two, or three of the hydrogen atoms in methylene groups in the foregoing formula substituted by an equivalent number of methyl groups, provided that the total number of carbon atoms within the branched fatty acid remains within the range of 10-30.

Some examples of linear unsaturated fatty acids containing a single carbon-carbon double bond include cis-2-decenoic acid, trans-2-decenoic acid, cis-3-decenoic acid, trans-3-decenoic acid, 9-decenoic acid, cis-2-undecenoic acid, trans-2-undecenoic acid, cis-2-dodecenoic acid, trans-2-dodecenoic acid, cis-2-tetradecenoic acid, trans-2-tetradecenoic acid, cis-9-tetradecenoic acid (myristoleic acid), cis-2-hexadecenoic acid, trans-2-hexadecenoic acid, cis-9-hexadecenoic acid (palmitoleic acid), cis-6-hexadecenoic acid (sapienic acid), cis-9-octadecenoic acid (oleic acid), trans-11-octadecenoic acid (vaccenic acid), trans-9-octadecenoic acid (elaidic acid), trans-2-eicosenoic acid, cis-2-eicosenoic acid, and cis-13-docosenoic acid (erucic acid). Some examples of linear unsaturated fatty acids containing more than one carbon-carbon double bond include cis,cis-9,12-octadecadienoic acid (linoleic acid), trans,trans-9,12-octadecadienoic acid (linolelaidic acid), trans,trans-9,11-conjugated linoleic acid, all-cis-9,12,15-octadecatrienoic acid (alpha-linolenic acid), all-cis-11,14,17-eicosatrienoic acid, and all-cis-5,8,11,14-eicosatetraenoic acid. Some examples of unsaturated fatty acids containing one or two carbon-carbon triple bonds include 9-decynoic acid, 2-decynoic acid, 5-hexadecynoic acid, 7-hexadecynoic acid, 5,7-hexadecadiynoic acid, 9-octadecynoic acid, 17-octadecynoic acid, 2-eicosynoic acid, 11-eicosynoic acid, 13-eicosynoic acid, 10-pentacosynoic acid, 10,12-pentacosadiynoic acid, 10-tricosynoic acid, and 10,12-tricosadiynoic acid. In some embodiments, the alkynyl bond is specifically located at the 2-position.

Some examples of branched unsaturated fatty acids containing a single carbon-carbon double bond include cis-9-methyl-2-decenoic acid, trans-9-methyl-2-decenoic acid, cis-9-methyl-7-decenoic acid, cis-4,8-dimethyl-4-decenoic acid, cis-4,8-dimethyl-10-hydroxy-4-decenoic acid, cis-5-methyl-2-undecenoic acid, trans-5-methyl-2-undecenoic acid, cis-11-methyl-2-dodecenoic acid, trans-11-methyl-2-dodecenoic acid, cis-10-methyl-2-dodecenoic acid, trans-10-methyl-2-dodecenoic acid, cis-5-methyl-2-tridecenoic acid, trans-5-methyl-2-tridecenoic acid, trans-2,5-dimethyl-2-tridecenoic acid, trans-7-methyl-6-hexadecenoic acid, trans-14-methyl-8-hexadecenoic acid, cis-17-methyl-6-octadecenoic acid, 3,7-dimethyl-6-octenoic acid, and cis-2,4,6-trimethyl-2-tetracosenoic acid. Some examples of branched unsaturated fatty acids containing more than one carbon-carbon double bond include cis,cis-4,8-dimethyl-4,7-decadienoic acid, cis-4,8-dimethyl-4,8-decadienoic acid, trans-5,9-dimethyl-4,8-decadienoic acid, cis,cis-11-methyl-2,5-dodecadienoic acid, all-trans-3,7,11-trimethyl-2,4-dodecadienoic acid, and cis,cis-17-methyl-9,12-octadecadienoic acid.

In some embodiments, the unsaturated fatty acid is more specifically a cis-2-unsaturated fatty acid of the following formula:

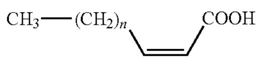

(1)

In Formula (1) above, n is an integer of 6-26, which corresponds to a number of carbon atoms of 10-30. In different embodiments, n may be, for example, 10, 12, 14, 16, 18, 20, 22, 24, or 26, or a value within a range bounded by any two of the foregoing values (e.g., 8-26, 8-24, 8-22, 8-20, 10-26, 10-24, 10-22, 10-20, 12-26, 12-24, 12-22, 12-20, 12-18, 14-20, or 14-18). Notably, the cis-2-unsaturated fatty acid shown in Formula (1) optionally includes a second carbon-carbon double bond resulting from removal of two hydrogen atoms on adjacent carbon atoms. In some embodiments, the cis-2-unsaturated fatty acid shown in Formula (1) optionally includes a third or fourth carbon-carbon double bond (resulting from removal of two pairs or three pairs, respectively, of hydrogen atoms on equivalent pairs of adjacent carbon atoms). Branched unsaturated fatty acids according to Formula (1) contain precisely or at least one, two, or three of the hydrogen atoms in methylene groups in Formula (1) substituted by an equivalent number of methyl groups, provided that the total number of carbon atoms within the branched fatty acid remains within the range of 10-30.

Several examples of cis-2-unsaturated fatty acids within the scope of Formula (1), including linear, branched, mono-unsaturated and polyunsaturated, have been provided above. Some examples of these types of fatty acids include cis-2-decenoic acid (i.e., (Z)-dec-2-enoic acid), trans-2-decenoic acid, cis-9-methyl-2-decenoic acid, trans-9-methyl-2-decenoic acid, cis-2-undecenoic acid, trans-2-undecenoic acid, cis-5-methyl-2-undecenoic acid, trans-5-methyl-2-undecenoic acid, cis-2-dodecenoic acid (i.e., (Z)-dodec-2-enoic acid), trans-2-dodecenoic acid, cis-11-methyl-2-dodecenoic acid, trans-11-methyl-2-dodecenoic acid, cis-10-methyl-2-dodecenoic acid, trans-10-methyl-2-dodecenoic acid, cis-5-methyl-2-tridecenoic acid, trans-5-methyl-2-tridecenoic acid, trans-2,5-dimethyl-2-tridecenoic acid, cis-2-tetradecenoic acid, trans-2-tetradecenoic acid, cis-2-hexadecenoic acid (i.e., (Z)-hexadec-2-enoic acid), cis-2-icosenoic acid (i.e., (Z)-icos-2-enoic acid), cis-2,4,6-trimethyl-2-tetracosenoic acid, cis,cis-2,5-dodecadienoic acid, trans,trans-2,5-dodecadienoic acid, and cis,cis-11-methyl-2,5-dodecadienoic acid.

In some embodiments, any of the types of fatty acids described above may be substituted with an additional carboxylic acid (or carboxylate) group, or with a hydroxy group, by replacing one of the shown hydrogen atoms in the above formula with a carboxylic acid or hydroxy group. In the case of an additional carboxylic acid group, the fatty acid is a di-acid, e.g., sebacic acid, undecanedioic acid, dodecanedioic acid, tridecanedioic acid, 2-decenedioic acid, and dodec-2-enedioic acid (traumatic acid). Some examples of fatty acids containing a hydroxy group include 2-hydroxydecanoic acid, 3-hydroxydecanoic acid, 2-hydroxydodecanoic acid, 12-hydroxydodecanoic acid, 2-hydroxytetradecanoic acid, 2-hydroxyhexadecanoic acid, 10-hydroxy-2-decenoic acid (also known as queen bee acid), and 10-hydroxy-8-decynoic acid. The fatty acid may also include one or two oxo (keto) groups, as in 3-oxodecanoic acid or trans-9-oxo-2-decenoic acid. In some embodiments, an additional carboxylic acid group and/or hydroxy group, and/or any other additional substituent (e.g., oxo), is not present in the fatty acid. In some embodiments, the fatty acid contains solely a linear or branched saturated or unsaturated hydrocarbon portion and a single carboxylic acid group.

The fatty acid can be obtained or produced by any suitable method. In one embodiment, the fatty acid is extracted from a microbe, such as some species of Proteobacteria, which use certain fatty acids, known as diffusible signaling factors (DSFs) for quorum sensing. In another embodiment, the fatty acid is obtained commercially. In other embodiments, the fatty acid is produced by synthetic means known in the art, e.g., M. B. Richardson et al., Beilstein *J. Org. Chem.*, 9, 1807-1812, 2013 (doi:10.3762/bjoc.9.210); M. S. J.-W. Song et al., *Angew. Chem. Intl. Ed.*, 52(9), 2013 (doi.org/10.1002/anie. 201209187), H. Sprecher, *Prog. Chem. Fats other Lipids*, 15, 219-254 (doi.org/10.1016/0079-6832(77)90009-X), and H. L. Ngo et al., *JAOCS*, 83(7), 629-634, July 2006 (doi.org/10.1007/s11746-006-1249-0), the entire contents of which are herein incorporated by reference. In other embodiments, the fatty acid is produced by gene manipulation of plants or plant cells, such as described in U.S. Pat. Nos. 6,051,754 and 6,075,183, the contents of which are herein incorporated by reference. In yet other embodiments, the fatty acid is produced in recombinant cells, such as yeast or plant cells, as described in U.S. Pat. No. 7,807,849, the contents of which are herein incorporated by reference.

As mentioned above, in the composition, the fatty acid may be dissolved or suspended in a pharmaceutically acceptable carrier, which is typically a liquid or semi-solid (e.g., gel or wax) under typical conditions encountered when a subject is administered the composition. In the latter case, the composition may be referred to as a "pharmaceutical composition". The fatty acid may alternatively be dissolved or suspended in a feed or enteric formulation for a human or animal subject. The feed or enteric formulation may be any food normally consumed by a human or animal subject, e.g., yogurt or nutritional shake for a human, and grain- or grass-based meal for poultry and cattle. The phrase "pharmaceutically acceptable" refers herein to those compounds, materials, compositions, and/or dosage forms which are, within the scope of sound medical judgment, suitable for administration to a subject. Each carrier should be "acceptable" in the sense of being compatible with the other ingredients of the formulation and physiologically safe to the subject. Any of the carriers known in the art can be suitable herein depending on the mode of administration.

Some examples of pharmaceutically acceptable liquid carriers include alcohols (e.g., ethanol), glycols (e.g., propylene glycol and polyethylene glycols), polyols (e.g., glycerol), oils (e.g., mineral oil or a plant oil), paraffins, and aprotic polar solvents acceptable for introduction into a mammal (e.g., dimethyl sulfoxide or N-methyl-2-pyrrolidone) any of which may or may not include an aqueous component (e.g., at least, above, up to, or less than 10, 20, 30, 40, or 50 vol % water). Some examples of pharmaceutically acceptable gels include long-chain polyalkylene glycols and copolymers thereof (e.g., poloxamers), cellulosic and alkyl cellulosic substances (as described in, for example, U.S. Pat. No. 6,432,415), and carbomers. The pharmaceutically acceptable wax may be or contain, for example, carnauba wax, white wax, bees wax, glycerol monostearate, glycerol oleate, and/or paraffins, such as described in, for example, PCT International Publication WO2009/117130.

In some embodiments, the pharmaceutically acceptable carrier is or includes a capsule that houses the fatty acid. The term "capsule," as used herein, refers to both macroscopic capsules (e.g., commercial gel capsules) designed for oral administration, as well as microscopic or molecular compartments, such as micelles and liposomes. Macroscopic gel capsules, which may be soft-shelled or hard-shelled, are commonly used in numerous over-the-counter medications, supplements, and neutraceuticals and are typically primarily composed of a gelling agent, such as gelatin or a polysaccharide (e.g., starch, cellulose, or carrageenan).

In some embodiments, the capsule housing the fatty acid is a liposome. As well known in the art, a liposome has a lipid bilayer structure formed by the ordered assembly of amphiphilic molecules. In an aqueous environment, the liposome possesses a hydrophobic layer having inner and outer surfaces that are hydrophilic. Thus, if the drug is suitably hydrophilic, the drug may be encapsulated in an interior portion of the liposome or may be attached to an outer surface thereof, whereas, if the drug is suitably hydrophobic, the drug may be intercalated within the hydrophobic layer of the liposome. The liposome can have any of the compositions well known in the art, such as a phosphatidylcholine phospholipid composition, phosphatidylethanolamine phospholipid composition, phosphatidylinositol phospholipid composition, or phosphatidylserine phospholipid composition. Liposomal forms of the pharmaceutical composition described herein can be produced by methods well known in the art.

In other embodiments, the capsule housing the fatty acid is a micelle. As well known in the art, a micelle is distinct from a liposome in that it is not a bilayer structure and possesses a hydrophobic interior formed by the ordered interaction of amphiphilic molecules. Thus, a drug of sufficient hydrophobicity may be intercalated or encapsulated within the micellular structure, while a drug of sufficient hydrophilicity may be attached to the outer surface of the micelle. The micelle can be constructed of any of the numerous biocompatible compositions known in the art, such as a PEG-PLA or PEG-PCL composition. The micelle may further be a pH-sensitive or mucous-adhesive micelle as well known in the art. An overview of micellular compositions and methods for producing them is provided in, for example, W. Xu et al., *Journal of Drug Delivery, Article* 340315, 2013 (doi.org/10.1155/2013/340315), the contents of which are herein incorporated by reference.

The fatty acid is typically present in the composition in a concentration of 100 nM to 20 mM. In different embodiments, the fatty acid is present in the composition in a concentration of 100 nm, 200 nM, 500 nM, 1000 nM (1 μM), 2 μM, 5 μM, 10 μM, 50 μM, 100 μM, 200 μM, 500 μM, 1000 μM (1 mM), 2 mM, 5 mM, 10 mM, or 20 mM, or a concentration within a range bounded by any two of the foregoing values (e.g., 1 μM to 20 mM).

In some embodiments, the composition contains solely the fatty acid and one or more solvents, and optionally, a capsule housing, as described above. In other embodiments, the composition includes one or more additional components. The additional component may be, for example, a pH buffering agent, mono- or poly-saccharide (e.g., lactose, glucose, sucrose, trehalose, lactose, or dextran), preservative, electrolyte, surfactant (for aiding dissolution of the fatty acid), or antimicrobial. If desired, a sweetening, flavoring, or coloring agent may be included. Other suitable excipients can be found in standard pharmaceutical texts, e.g. in "Remington's Pharmaceutical Sciences", The Science and Practice of Pharmacy, 19th Ed. Mack Publishing Company, Easton, Pa., 1995. The composition may or may not also include one or more auxiliary active substances conventionally used in the treatment of *Salmonella* infection. The one or more auxiliary active substances may be, for example, an antidiarrheal agent (e.g., loperamide) or antibiotic (e.g., amoxicillin, ampicillin, trimethoprim-sulfamethoxazole, cefotaxime, or ceftriaxone).

In some embodiments, the composition contains a single fatty acid, such as any of the saturated, unsaturated, linear, or branched fatty acids described above. In other embodiments, the composition includes a combination (e.g., two, three, or more) fatty acids, such as two or more different saturated fatty acids, two or more different unsaturated fatty acids, a saturated fatty acid in combination with an unsaturated fatty acid, two or more linear fatty acids, two or more branched fatty acids, or a linear fatty acid in combination with a branched fatty acid.

In another aspect, the invention is directed to a method for treating (e.g., inhibiting or preventing) *Salmonella* infection in a subject, wherein the subject may be human or animal. The animal may be, for example, fowl (e.g., chicken, duck, or turkey), reptile (e.g., turtle, lizard, or snake), or mammal (e.g., cow, goats, sheep, or pig). The term "infection," as used herein, is defined as the *Salmonella* invasion of the intestinal epithelium. The method involves enterally administering a pharmaceutically acceptable amount of one or more of the above described long chain fatty acids to inhibit or prevent *Salmonella* invasion of the intestinal epithelium in the subject. As further discussed below, the long chain fatty acid inhibits or prevents *Salmonella* invasion by repressing expression of at least one *Salmonella* invasion gene, e.g., AraC-type transcriptional regulators in and outside of pathogenicity islands. The fatty acid is typically within a pharmaceutically acceptable carrier or food (enteric) formulation when administered, although the present disclosure considers embodiments in which the fatty acid is administered by itself, i.e., not within a pharmaceutically acceptable carrier, particularly in the case where the fatty acid is itself a liquid or semi-solid.

The fatty acid is administered to the subject by any of the enteral means known in the art. In a first embodiment, the enteral administration is oral administration, i.e., through the mouth and esophagus. In a second embodiment, the enteral administration is naso-gastric or naso-enteric administration, i.e., bypassing the mouth and delivering contents to the stomach or small intestine via the nasal passages. In a third embodiment, the enteral administration is achieved by an artificial opening leading to the stomach or one of the intestines, e.g., via a gastrostomy tube (G-tube) or jejunostomy tube (J-tube). In some embodiments, the fatty acid is incorporated into a nutritive or electrolyte formulation being administered to the subject.

In some embodiments, the subject has already contracted *Salmonella* when the subject is administered the long chain fatty acid, in which case the method of treating functions to inhibit or prevent *Salmonella* invasion of the intestinal epithelium in the subject, thereby inhibiting or preventing infection of the subject by *Salmonella*. In other embodiments, the subject has not contracted *Salmonella* when the subject is administered the long chain fatty acid, in which case the method of treating functions as a preventative measure to inhibit or prevent *Salmonella* invasion of the intestinal epithelium in the subject, should the subject contract *Salmonella*. The phrase "inhibits *Salmonella* invasion," as used herein, refers to a reduction in the extent of *Salmonella* invasion of the intestinal epithelium in a subject compared to either an existing level of *Salmonella* invasion of the subject when first administered the fatty acid or compared to a level of *Salmonella* invasion of in a control subject not treated. The phrase "prevents *Salmonella* invasion," as used herein, refers to a stoppage of *Salmonella* invasion of the intestinal epithelium in the case where *Salmonella* invasion has already started, or the phrase refers to prevention of *Salmonella* invasion of the intestinal epithelium in the case where *Salmonella* invasion has not yet started. The phrases "inhibits *Salmonella* invasion" and "prevents *Salmonella* invasion" are also meant to be synonymous with the respective phrases "inhibits *Salmonella* infection" and "prevents *Salmonella* infection" wherein the inhibition or prevention of infection can be assessed according to the extent of symptoms normally associated with *Salmonella* infection, e.g., nausea, vomiting, abdominal or intestinal cramping, diarrhea, fever, and/or fluid loss.

The pharmaceutically effective amount of the fatty acid is dependent on the severity and responsiveness of the *Salmonella* being treated or prevented, with the course of treatment or prevention lasting from several days to weeks or months, or until a cure is effected or an acceptable diminution of the disease state is achieved. Optimal dosing schedules can be calculated from measurements of drug accumulation in the body of the patient. The administering physician can determine optimum dosages, dosing methodologies, and repetition rates. The dosing can also be modified based on the detected level of *Salmonella* infection, level of invasion, or level of susceptibility or fragility of the patient (e.g., based on age and overall health, particularly immune system health). The fatty acid is typically administered in a dosage of 50 mg to 2000 mg daily for at least one, two, or three days. In different embodiments, depending on the above and other factors, a suitable dosage of the active ingredient may be precisely, at least, or no more than, for example, 50 mg, 100 mg, 200 mg, 300 mg, 400 mg, 500 mg, 600 mg, 700 mg, 800 mg, 900 mg, 1000 mg, 1200 mg, 1500 mg, 1800 mg, or 2000 mg, per 50 kg, 60 kg, or 70 kg adult, or a dosage within a range bounded by any of the foregoing exemplary dosages. Depending on these and other factors, the composition is administered in the indicated dosage by any suitable schedule, e.g., once, twice, or three times a day for a total treatment time of one, two, three, four, or five days, and up to, for example, one, two, three, or four weeks or months. The indicated dosage may alternatively be administered every two or three days, or per week. Alternatively, or in addition, the pharmaceutical composition is administered until a desired change is evidenced.

In some embodiments, the treatment method involves administering only one or more of the fatty acids described above as the sole active agent for treating *Salmonella* infection. In other embodiments, the treatment method involves co-administering one or more other active agents known in the art for treating *Salmonella* infection. The active agent may be an agent that disrupts growth and reproduction of *Salmonella*, or the active agent may be an agent that treats one or more symptoms associated with *Salmonella* infection. The one or more other active agents may be, for example, an antidiarrheal agent (e.g., loperamide), anti-emetic, anti-pyretic, or antibiotic, such as amoxicillin, ampicillin, trimethoprim-sulfamethoxazole, cefotaxime, or ceftriaxone. In a first instance, the co-administration is accomplished by including one or more fatty acids in admixture with the one or more other active agents in the same pharmaceutical composition being administered. In a second instance, the co-administration is accomplished by administering one or more fatty acids separately from the one or more other active agents, i.e., at the same time or at different times. In some embodiments, the one or more other active agents function to desirably modulate or work in synergy with the one or more fatty acids.

Examples have been set forth below for the purpose of illustration and to describe the best mode of the invention at the present time. However, the scope of this invention is not to be in any way limited by the examples set forth herein.

EXAMPLES

Overview

Successful colonization by enteric pathogens is contingent upon effective interactions with the host and the resident microbiota. These pathogens thus respond to and integrate myriad signals to control virulence. Long-chain fatty acids repress the virulence of the important enteric pathogen *Salmonella enterica* by repressing AraC-type transcriptional regulators in pathogenicity islands. While several fatty acids are known to be repressive, it is herein shown that cis-2-unsaturated fatty acids, a rare chemical class used as diffusible signaling factors (DSFs) for quorum sensing by species of the Proteobacteria, are highly potent inhibitors of virulence functions. Unlike their role in quorum sensing, in which DSFs can signal through two-component regulators to modulate c-di-GMP turnover, it has herein been found that DSFs repressed virulence-gene expression of enteric pathogens by interacting with transcriptional regulators of the AraC family. In *S. typhimurium*, DSFs repressed the activity of HilD, HilC and RtsA, AraC-type activators essential to the induction of epithelial cell invasion, by preventing their interaction with target DNA and, in the specific case of HilD, inducing its rapid degradation by Lon protease.

Figure 1B:
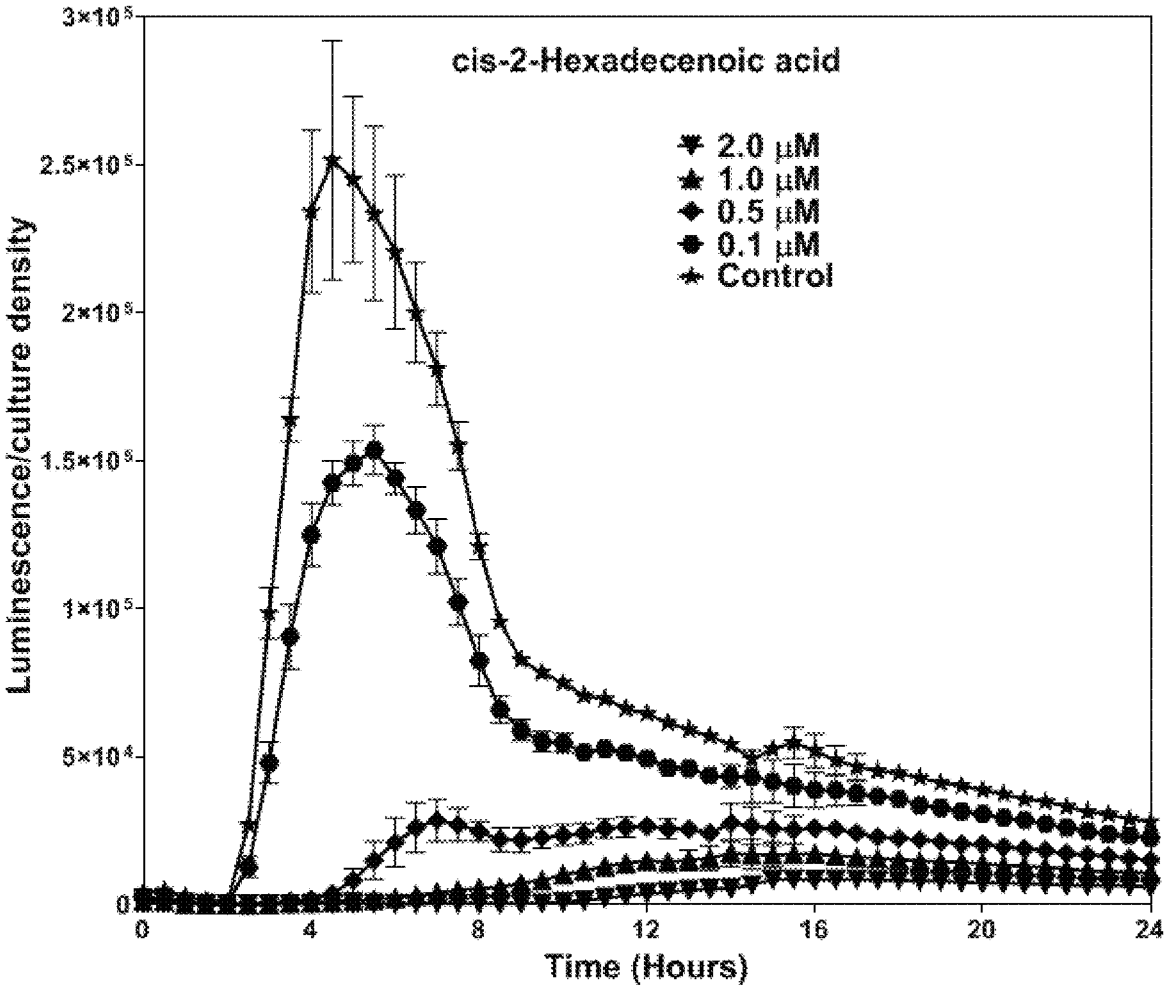
Figure 1C:
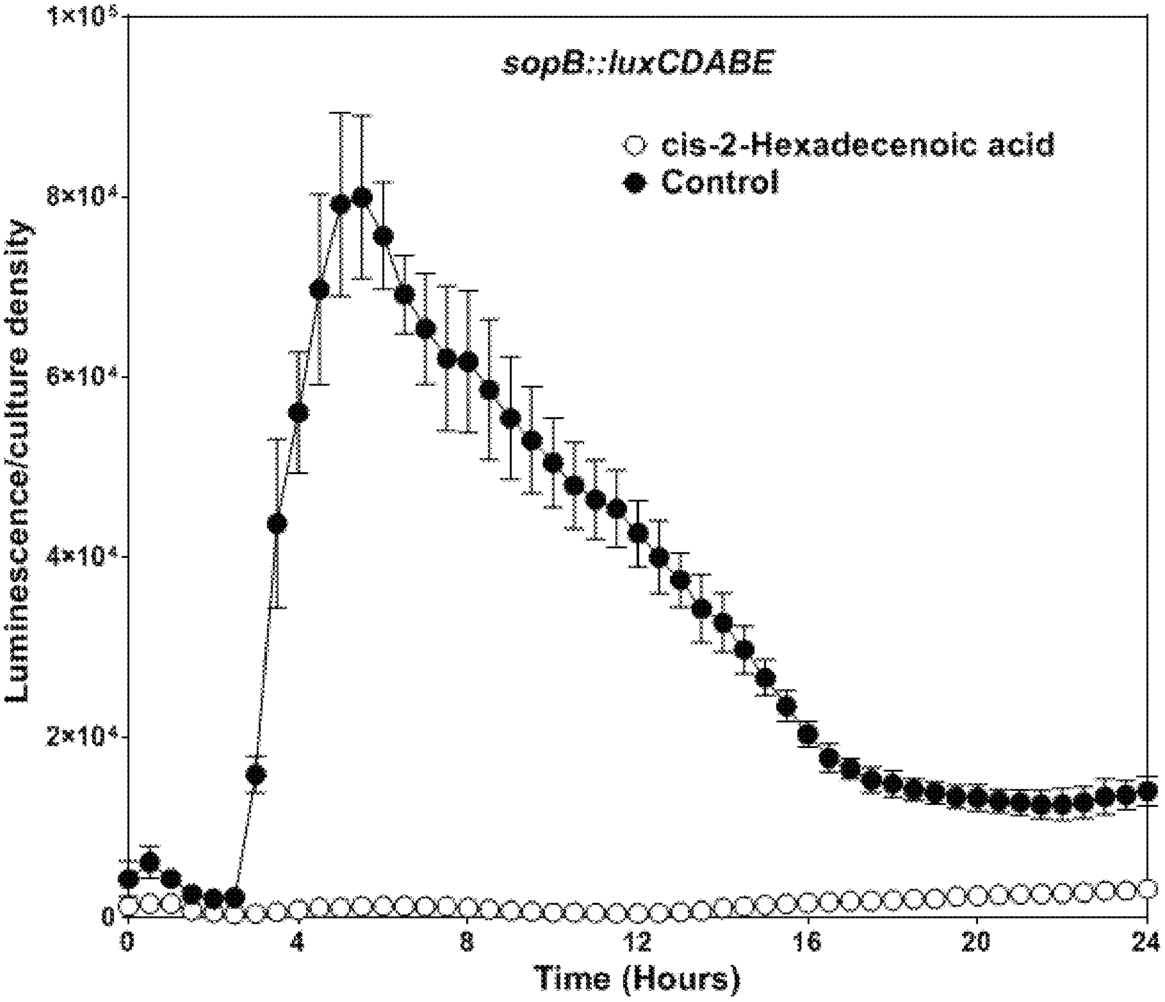
Figure 1D:
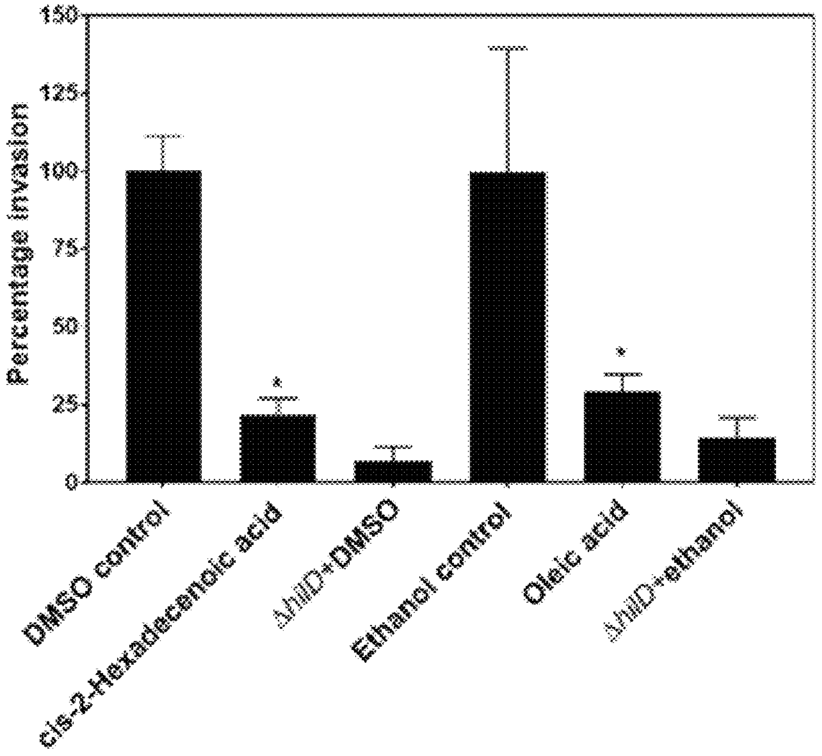
Figure 1E:
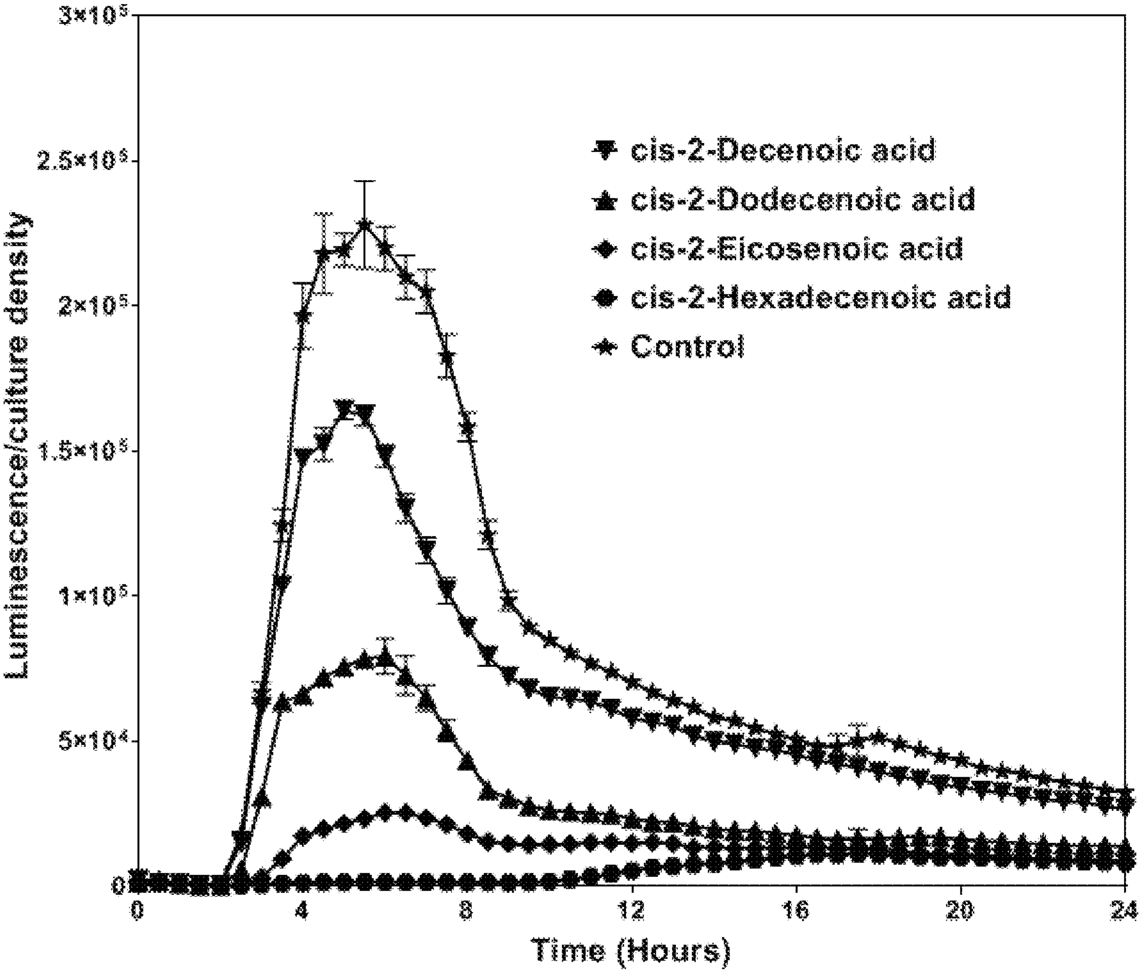
Figure 1F:
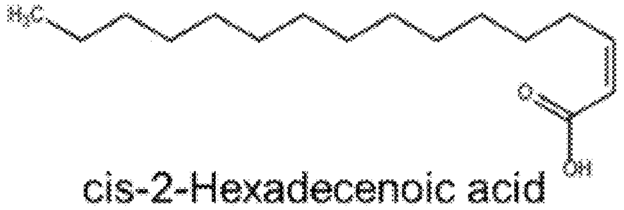
Figure 1F:
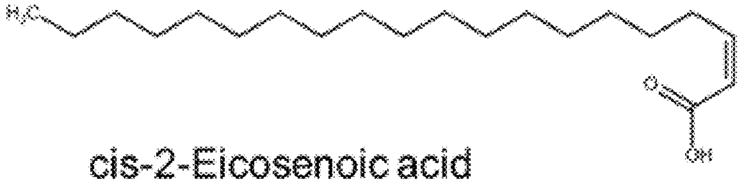
Figure 1F:
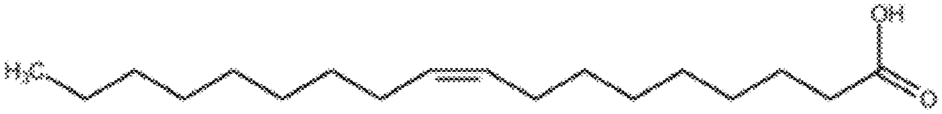

Cis-2-hexadecenoic acid (c2-HDA), also known as (Z)-hexadec-2-enoic acid (as shown in FIG. 1F), a DSF produced by *Xylella fastidiosa*, was herein found to be particularly potent among those tested for repressing the HilD-, HilC- and RtsA-dependent transcriptional regulator hilA and the type III secretion effector sopB by greater than 200- and 68-fold, respectively. Using the murine colitis model, c2-HDA significantly repressed invasion-gene expression by *Salmonella*, which indicates that the HilD-, HilC- and RtsA-dependent signaling pathway functions within the complex milieu of the animal intestine. Thus, it is likely that enteric pathogens respond to DSFs as interspecies signals to identify appropriate niches in the gut for virulence activation. The great potency of this DSF in repressing virulence can therefore be exploited to control the virulence of enteric pathogens.

In the intestinal milieu, pathogens engage in intricate interactions with the host and the microbiota that often lead to pathogen-colonization resistance (A. Jacobson et al., *Cell Host Microbe,* 24(2), 296-307 e7, 2018). To penetrate this colonization barrier, enteric pathogens regulate their virulence in response to gut environmental factors to ensure a timely activation and minimization of fitness costs (N. Kamada et al., *Science,* 336 (6086), 1325-1329, 2012). Therefore, many pathogens integrate a multitude of host and environmental signals with metabolic cues to optimize their virulence generation pathways (B. H. Abuaita et al., *Infect. Immun.,* 77(9):4111-4120, 2009). Many of these cues converge at the central transcriptional regulators of the AraC family in pathogenicity islands.

In *Salmonella*, the type III secretion system encoded by genes in *Salmonella* pathogenicity island 1 (SPI1) is controlled by the AraC-type transcriptional regulator HilD (R. L. Lucas et al., *J. Bacteriol.,* 183(9), 2733-245, 2001). Together with HilC and RtsA, also members of the AraC family, HilD forms a feed forward loop to induce hilA (C. D. Ellermeier et al., *Molecular Microbiology,* 57(3), 691-705, 2005). HilA activates the expression of genes encoding the needle complex and secreted effector proteins for invasion of epithelial cells (V. Bajaj et al., *Molecular Microbiology,* 18(4), 715-727, 1995). AraC-family transcriptional regulators control virulence in several pathogens, including type III secretion in *Shigella flexneri* (VirF) and *Yersinia pestis* (LcrF), and adhesion fimbriae in enterotoxigenic *Escherichia coli* (Rns) (M. T. Gallegos et al., *Microbiol. Mol. Biol. Rev.,* 61(4), 393-410, 1997).

Short- and long-chain fatty acids produced by the host and microbiota regulate virulence of the important enteric pathogen *Salmonella* by interacting with transcriptional regulators of the AraC family (C. C. Hung et al., *Molecular Microbiology,* 87(5), 1045-1060, 2013). Butyric acid and propionic acid, which exist in high concentrations in the gut, and oleic acid, which is abundant in bile, have been shown to regulate SPI1 through HilD (I. Gantois et al., *Appl. Environ. Microbiol.,* 72(1), 946-949, 2006 and C. C. Hung et al., Ibid.). While these transcriptional regulators have been shown to accommodate different sizes of fatty acids in vitro, the specific fatty acid repressors in the gut have not been identified.

A rare class of cis-2-unsaturated fatty acids is used by several bacterial pathogens of animals and plants to regulate quorum sensing-dependent behaviors, such as biofilm formation (J. M. Dow, *J. Appl. Microbiol.,* 122(1), 2-11, 2017). Termed diffusible signaling factors (DSFs), these include molecules with varying chain lengths and substituents. cis-11-methyl-2-dodecenoic acid was the first to be characterized from *Xanthomonas campestris* and later in *Stenotrophomonas maltophilia* (C. E. Barber et al., *Molecular Microbiology,* 24(3), 555-566, 1997); others shown to influence pathogenicity include cis-2-hexadecenoic acid (c2-HDA), cis-2-decenoic acid, and cis-2-dodecenoic acid, produced by *Xylella fastidiosa, Pseudomonas aeruginosa*, and *Burkholderia cenocepacia*, respectively (M. Ionescu et al., *MBio,* 7(4), 2016). Cis-2 unsaturation is required for the quorum-sensing activity of DSFs, as trans-isomers elicit little or no effect (L. H. Wang et al., *Mol. Microbial.,* 51(3), 903-912, 2004). Different species produce and respond to varied chain lengths, and cross-species activity of DSFs has been reported for several plant and animal pathogens (e.g., L. H. Wang et al., Ibid.). DSFs are produced by unique crotonases that encode both 3-hydroxyacyl-acyl carrier protein (ACP) dehydratase and an esterase activity (H. K. Bi et al., *Mol. Microbial.,* 83(4), 840-855, 2012). Signal recognition and transduction occurs differently among the species that produce them. In *X. fastidiosa*, DSFs are recognized through the outer membrane sensor kinases RpfC, which phosphorylates the phosphodiesterase regulator RpfG (Y. W. He et al., *Journal of Biological Chemistry,* 281(44), 33414-33421, 2006). In *B. cenocepacia*, however, DSFs are recognized by the cytoplasmic GGDEF-EAL domain protein RpfR, which encodes phosphodiesterase activity (Y. Y. Deng et al., *PNAS USA,* 109(38), 15479-15484, 2012). Both pathways regulate cyclic di-GMP turnover, which in turn regulates genes responsible for virulence and adaptation (H. Slater et al., *Mol. Microbial.,* 38(5), 9861003, 2000).

Herein is demonstrated that the DSF c2-HDA is a particularly potent inhibitor of enteric pathogen virulence-gene expression. c2-HDA acts by interacting with the central transcriptional regulators of SPI1, and most likely the VPI, both of which are required for successful gut colonization (Y. Dieye et al., *BMC Microbiology,* 9, 2009).

Materials and Methods

Strains. *Salmonella enterica* subsp. *enterica* serovar *Typhimurium* 14028s, and mutants thereof, were used throughout. Deletion mutants were constructed as previously described (K. A. Datsenko et al., *PNAS USA,* 97(12), 6640-6645, 2000). Briefly, PCR fragments of kanamycin and chloramphenicol resistance genes containing 40 base pair homology extensions flanking the gene of interest were generated using pKD4 and pKD3 plasmids. The PCR fragments were transformed into a strain expressing λ Red recombinase. Loss of the gene of interest was confirmed using PCR. Unmarked mutants were generated using a helper plasmid pCP20 carrying a gene encoding the FLP recombinase. Marked deletions and constructs were transferred using bacteriophage P22 transduction (N. L. Sternberg et al., *Methods Enzymol.,* 204, 18-43, 1991).

Luciferase assays. Strains carrying luxCDABE reporter fusions were grown overnight in LB with the necessary antibiotics. Overnight cultures were diluted 100-fold into M9 minimal medium with glucose, antibiotics and 1 mM nonanoic acid (added to repress SPI invasion gene expression to eliminate background luminescence), and grown overnight. The cultures were washed three times with PBS. Bacteria were inoculated at a starting $OD_{600}$ of 0.02 into 150 μL of LB containing 100 mM MOPS pH 6.7, the necessary antibiotics and compounds to be tested, in a sealed black-walled 96 well plate. Luminescence was measured every 30 minutes for 24 hours using a Biotek Synergy™ H1 microplate reader.

Invasion assay. Invasion was determined using a gentamicin-protection assay as previously described with modifications (C. Altier et al., *Mol. Microbiol.,* 35(3), 635-646, 2000). Bacteria were grown overnight in LB buffered with 100 mM HEPES, pH 8, in the presence of 20 μM cis-2-unsaturated fatty acid compounds. Overnight cultures were washed with PBS and ~$2\times10^6$ bacteria were added to 1 mL of HEp-2 cells to maintain a multiplicity of infection of 10. Plates were centrifuged for 10 minutes at 100×g and incubated for 1 hour at 37° C. Plates were then washed and gentamicin was added at a concentration of 20 μg/mL to the media. After 1 hour of incubation, cells were washed and lysed with 1% triton X-100. Lysates were plated on agar plates and recovered intracellular bacteria were counted. Percentage invasion in the presence of cis-2-unsaturated fatty acid compounds was calculated by comparing with the untreated cultures.

Methyl ester synthesis. Esters of c2-HDA and cis-2-eicosenoic acid were prepared by reacting methanolic acid with the compounds. The reaction mixture was refluxed at 80° C. for 30 minutes. Thin layer chromatography (TLC) was employed to monitor the progress of the esterification reaction, using ethyl acetate in hexane as the mobile phase. Phosphomolybdic acid was used to visualize product formation with gentle heating. The solvent was evaporated and the product lyophilized overnight before use.

Half-life assay. HilD half-life assays were performed as previously described (C. R. Eade et al., *Infection and Immunity,* 84(8), 2198-2208, 2016). Briefly, a strain with hilD under a controlled promoter ($P_{tetRA}$) and a C-terminal 3×FLAG tag construct was used. Cultures were grown overnight and then diluted 1:100 into LB containing 100 mM MOPS pH 6.7, 1 μg/mL tetracycline (for $P_{tetRA}$ induction) and 20 μM of fatty acid compounds to be tested. After 2.5 hours of growth, OD was adjusted to 1 for all cultures. Transcription and translation were halted by adding a cocktail of antibiotics. Cultures were incubated at 37° C. and samples were taken every 30 minutes for western blot analysis using an anti-FLAG antibody. The HilD-3×FLAG signal was quantified by detecting the density of bands using the UVP LS software (UVP LLC). Half-life was calculated as the difference in density between the time point zero and the last signal time point, as previously described (C. R. Eade, Ibid.).

HilD expression and purification. hilD was amplified and cloned into pCAV4, a modified T7 expression vector that introduces an N-terminal 6×His-NusA tag followed by a HRV 3C protease site. The construct was transformed into *E. coli* BL21(DE3). The expression strain was grown at 37° C. in terrific broth (TB) to $OD_{600}$ of 1 and induced with 0.3 mM IPTG. Induced cultures were grown overnight at 19° C. Cells were pelleted and re-suspended in nickel buffer (20 mM HEPES pH 7.5, 500 mM NaCl, 5% glycerol, 30 mM imidazole, and 5 mM β-mercaptoethanol). Cells were lysed by sonication and insoluble cell debris was removed by centrifugation at 13,000 rpm. The clarified supernatant was applied to a 5 mL Chelating HiTrap (GE) charged with nickel sulfate. The column was washed with nickel buffer and the protein was eluted with a 30 mM to 500 mM imidazole gradient. The pooled elutions were dialyzed overnight into heparin buffer (20 mM HEPES pH 7.5, 300 mM NaCl, 1 mM EDTA, 5% glycerol, and 1 mM DTT) in the presence of HRV 3C protease to remove the 6×His-NusA tag. Following dialysis, the protein was applied to a 5 mL Heparin HiTrap (GE), washed with heparin buffer, and eluted with a gradient of 300 mM to 1 M NaCl. HilD was then concentrated and injected onto a Superdex™ 200 10/300 sizing column (GE) equilibrated in HilD storage buffer (20 mM HEPES pH 7.3, 500 mM KCl, and 1 mM DTT). The final concentration of purified HilD was 10-20 mg/mL.

Electrophoretic mobility shift assays (EMSAs). EMSAs were performed as previously described (Y. A. Golubeva et al., *M Bio,* 7(1), 2016). Briefly, 10 nM of hilA promoter DNA was mixed with 150 μM HilD, HilC or RtsA in a binding buffer containing 20 mM KCl, 1% glycerol, 1 mM DTT, 0.04 mM EDTA, 0.05% Tergitol™ NP-40 and 20 mM HEPES, pH 7.3. cis-2-hexadecenoic acid was tested at concentrations of 1 to 200 Binding was performed at room temperature for 20 minutes. Samples were separated on 6% Novex® TBE DNA retardation gels, and DNA was stained using SYBR® green (Invitrogen).

Animal experiments. Female C57BL/6 mice, 6-7 weeks old, were provided with c2-HDA at a concentration of 1.5 mM, or the vehicle control (Solutol® HS 15), as their sole drinking water source throughout the experiment. Mice were inoculated by gastric gavage with 20 mg of streptomycin 24 hours after the introduction of treated water. Bacterial strains were grown overnight in M9 minimal media supplemented with 0.2% glucose. Cultures were washed twice and re-suspended in PBS. Mice were inoculated with ~$10^8$ bacteria by gastric gavage 24 hours after treatment with streptomycin. Mice were euthanized 1 day after *Salmonella* infection using carbon dioxide according to the American Veterinary Medical Association guidelines, and cecal contents were collected.

Flow cytometry. Cecal contents were diluted into 5 mL PBS, vortexed for 2 minutes and filtered with 5 μM filters to remove debris. Recovered cells were pelleted and re-suspended in 1 ml 4% paraformaldehyde in 1×PBS. Cells were fixed for 30 minutes at 4° C., pelleted to remove paraformaldehyde and re-suspended in PBS. Flow cytometry was performed as previously described (C. R. Eade et al., *Infection and Immunity,* 87(1), 2019). Recovered cells were analyzed for BFP and GFP expression using an Attune™ analyzer NxT flow cytometer (Invitrogen). *Salmonella* was identified by BFP expression, and GFP was used to monitor SPI1 expression. Data was analyzed using the FlowJo™ 10.6.1 software (FlowJo LLC).

Statistical analysis. Means of treated and untreated samples were compared using Student's t-test.

Experimental Results

The diffusible signaling factor c2-HDA has herein been found to be a highly potent inhibitor of virulence-gene expression. An aim of the present research was to identify related chemicals that could potently inhibit invasion-gene expression and determine the mechanisms by which they repress these genes. To this end, the present research tested the efficacy of a rare class of fatty acids with a characteristic cis-2-unsaturation, termed DSFs (e.g., J. M. Dow et al., Ibid.). A *Salmonella* strain carrying a hilA::luxCDABE reporter fusion was used to monitor effects of cis-2-unsaturated fatty acids on SPI1-encoded invasion-gene expression, as HilA directly activates expression of genes responsible for the production of the type III secretion complex and effector proteins (e.g., V. Bajaj et al., Ibid.). When supplied to cultures at a concentration of 5 μM, c2-HDA significantly repressed hilA expression (>200-fold) to a level that was undetectable in the present assay. For comparison, oleic acid, which has been shown to repress SPI1 through its effects on HilD, slightly repressed hilA (1.3-fold) at this same concentration (FIG. 1A). Notably, this chemical did not impair bacterial growth. Moreover, c2-HDA proved to maintain its potency at a range of concentrations, repressing 80-fold at 1 μM and significantly inhibiting hilA expression (39%) at 100 nM (FIG. 1B).

The mechanisms by which DSFs repress virulence in *Salmonella* were also investigated. The present research first tested whether c2-HDA repressed genes encoding type III secretion effector proteins using a sopB::luxCDABE reporter fusion, as the effector protein SopB is essential for invasion of epithelial cells (M. Raffatellu et al., *Infection and Immunity,* 73(1), 146-154, 2005). c2-HDA significantly repressed sopB expression by 68-fold (FIG. 1C). The data suggests that the repression of SPI1 by c2-HDA leads to transcriptional inhibition of effector protein genes. Thus, the present research next tested the invasion competency of bacteria grown in the presence of the c2-HDA. Overnight growth of *Salmonella* in the presence of c2-HDA significantly decreased its invasion of HEp-2 cells by 78% compared to untreated cultures, while oleic acid reduced invasion by 70% at the same concentration (FIG. 1D). Together, the data indicate that c2-HDA represses invasion-gene expression and the ability of *Salmonella* to invade epithelial cells.

Figure 2A:
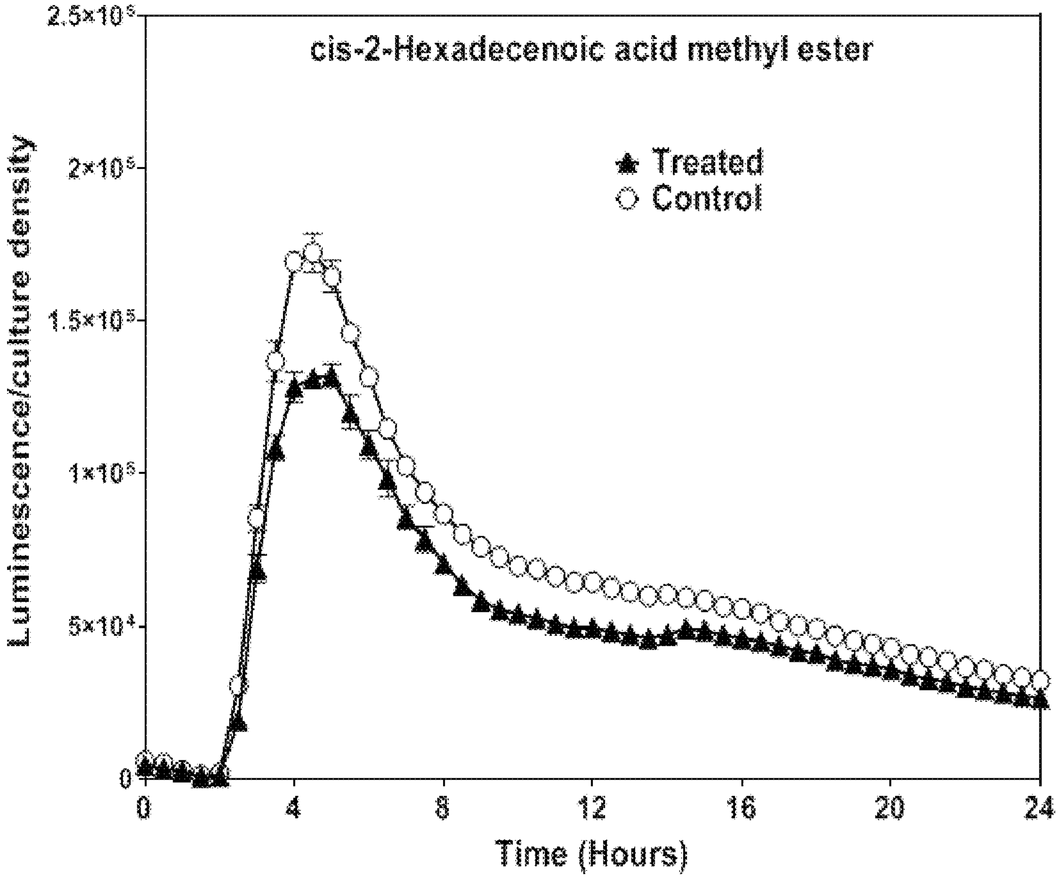
FIGS. 2A-2B. Luminescence vs. time data showing that methylation of the carboxyl end reduces the potency of cis-2-unsaturated fatty acids. A strain carrying a hilA::lux reporter plasmid was grown in the presence of: 20 μM cis-2-hexadecenoic acid methyl ester (data shown in FIG. 2A) and 40 μM cis-2-eicosenoic acid methyl ester (data shown in FIG. 2B). Expression of hilA is reported as mean luminescence normalized to bacterial culture density. Error bars represent standard deviations of 5 replicates. The control culture contained the vehicle only at identical concentration to the treated culture.
Figure 2B:
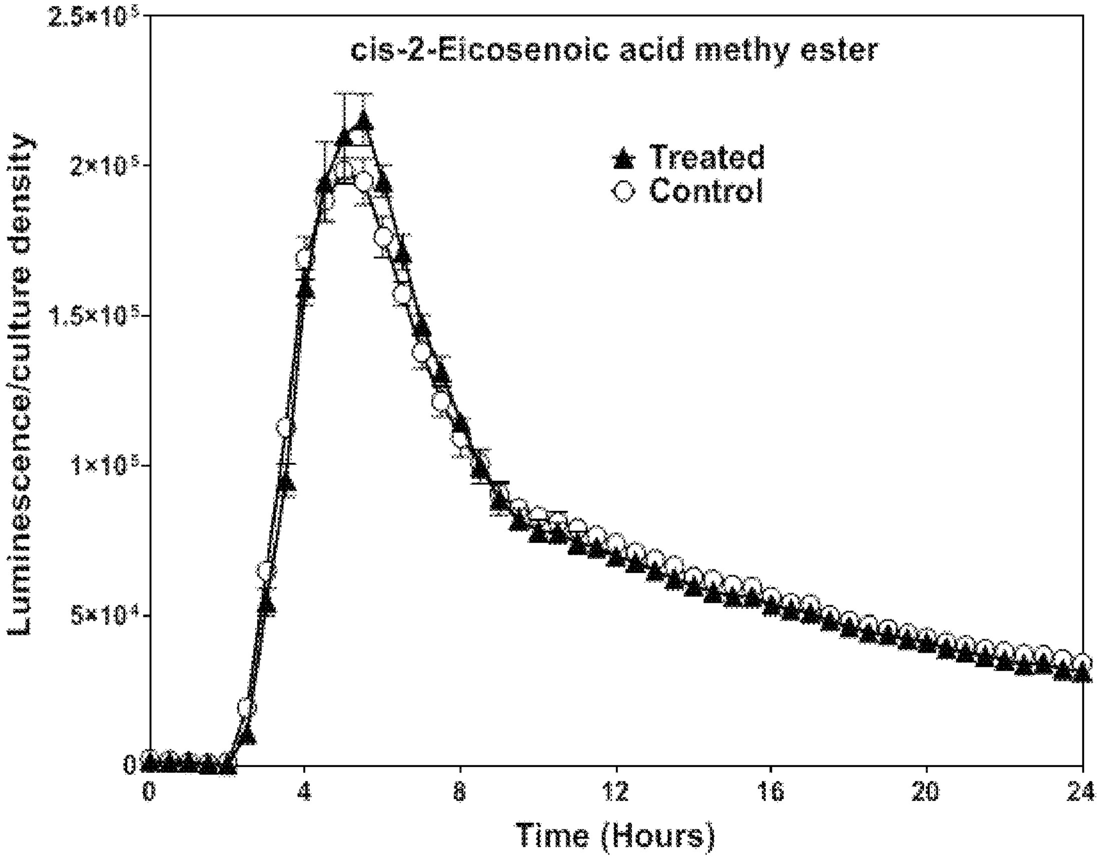

The cis-2-unsaturation of DSFs is the essential signature for quorum signaling, as trans-2-unsaturated isomers have minimal effects (L. H. Wang et al., *Mol. Microbiol.,* 51(3), 903-912, 2004). The present research thus tested the potency of trans-2-hexadecenoic acid in repressing hilA. The trans-isomer was 31-fold less potent in repressing hilA than was the cis-isomer, which indicates a specificity of the cis-2-unsaturaturation orientation (FIG. 1A). The present research next determined whether the chain length of DSFs was important for their potency by testing the ability of cis-2-unsaturated compounds of varying lengths to repress hilA. Among the tested DSFs, the 16-carbon c2-HDA, produced by the plant pathogen *X. fastidiosa* (M. Ionescu et al., Ibid.), was the most potent, significantly reducing hilA expression by 159-fold (FIG. 1E). The 12-carbon DSF cis-2-dodecenoic acid, produced by *B. cenocepacia* (C. Boon et al., *ISME Journal,* 2(1), 27-36, 2008), also significantly reduced hilA expression, but to a much lesser extent, by 3-fold. The least potent was the 10-carbon cis-2-decenoic acid, a product of *P. aeruginosa* (C. Boon et al., Ibid.), which slightly reduced hilA expression by 28%. Additionally, the 20-carbon cis-2-eicosenoic acid (depicted in FIG. 1F), unknown as a DSF but differing from recognized DSFs by only its length, repressed hilA by 10-fold (FIG. 1E). Thus, of these related compounds, both the chain length and the orientation of its double-bond make c2-HDA most effective in repressing hilA. The present research next sought to determine whether the carboxyl end of the fatty acids played any role in the repression of invasion genes. Methyl esters of c2-HDA and cis-2-eicosenoic acid were found not to significantly repress hilA expression, which indicates the importance of the terminal carboxyl group for the activity of these cis-2-unsaturated fatty acids (FIGS. 2A and 2B).

Figure 3A:
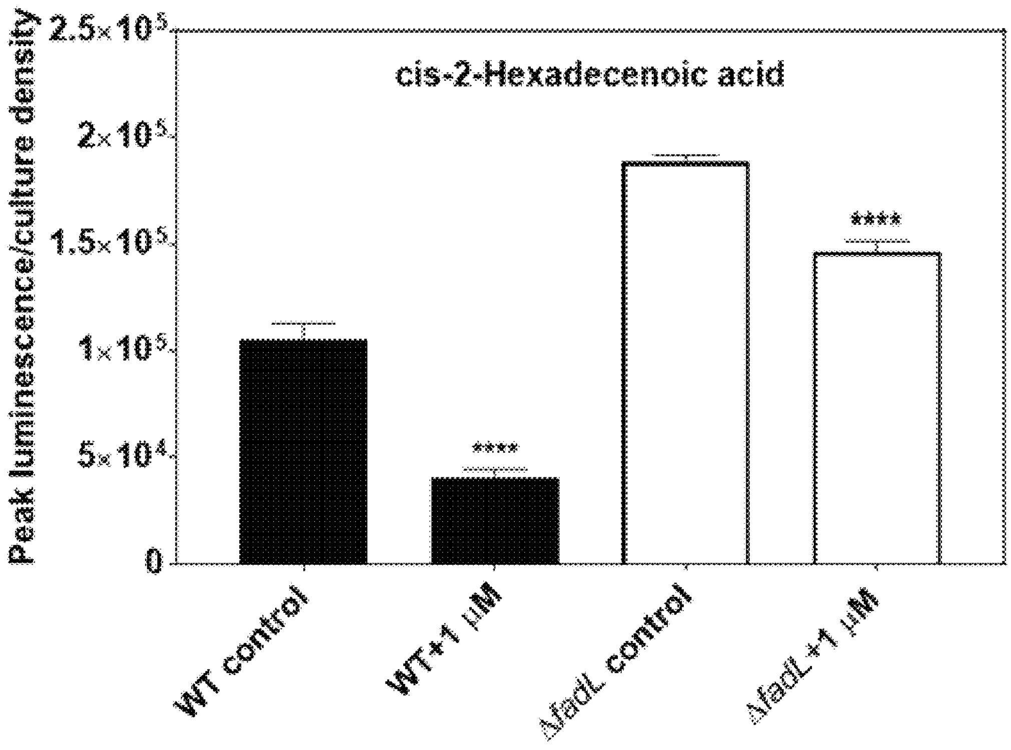
FIGS. 3A-3B: Data showing that repressive effects of cis-2-hexadecenoic acid (the selected DSF) are dependent on the fatty acid transporter but independent of β-oxidation.

In some bacteria, DSFs signal through two-component systems that utilize a trans-membrane sensory kinase, and thus, the perception of the signals occurs extracellularly (J. M. Dow, Ibid.). This raised the question of whether DSFs act extracellularly in *Salmonella*, or whether they must instead be transported into the bacterial cytoplasm. The present research thus determined whether c2-HDA continued to repress hilA in the absence of the long-chain fatty acid transporter FadL. In a FadL null mutant, c2-HDA, tested at a concentration of 1 μM, was 39% less potent in repressing hilA compared to the wild type (FIG. 3A). Therefore, it is likely that, in *Salmonella*, cis-2-unsaturated fatty acids act in the cytoplasm to repress invasion, as has been reported for oleic acid (Y. A. Golubeva et al., Ibid.).

Figure 3B:
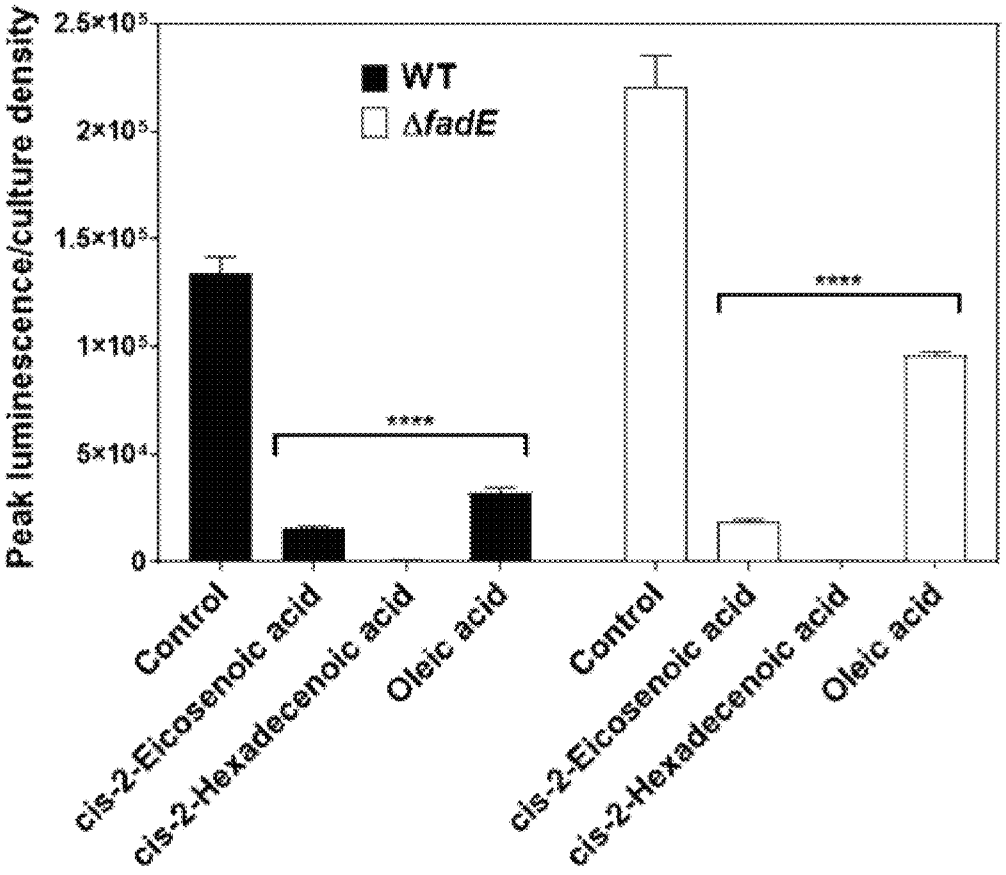

The results above suggest that a precise chemical structure is necessary for the activity of cis-2-unsaturated fatty acids on SPI1 virulence genes. Thus, it is herein hypothesized that these compounds repress directly, and not through degradation products. To test this, the present research disrupted the β-oxidation pathway, through which fatty acid compounds are degraded, using an acyl-CoA dehydrogenase (fadE) null mutant, interrupting the conversion of acyl-CoA to 2-enoyl-CoA (the first step of β-oxidation), and thus, the degradation of fatty acyl-CoA esters (J. W. Campbell et al., *Journal of Bacteriology,* 184(13), 3759-3764, 2002). Cis-2-unsaturated fatty acids continued to repress hilA in the absence of fadE, as has been reported for oleic acid, suggesting that their effects are independent of degradation via β-oxidation (FIG. 3B).

Figure 4A:
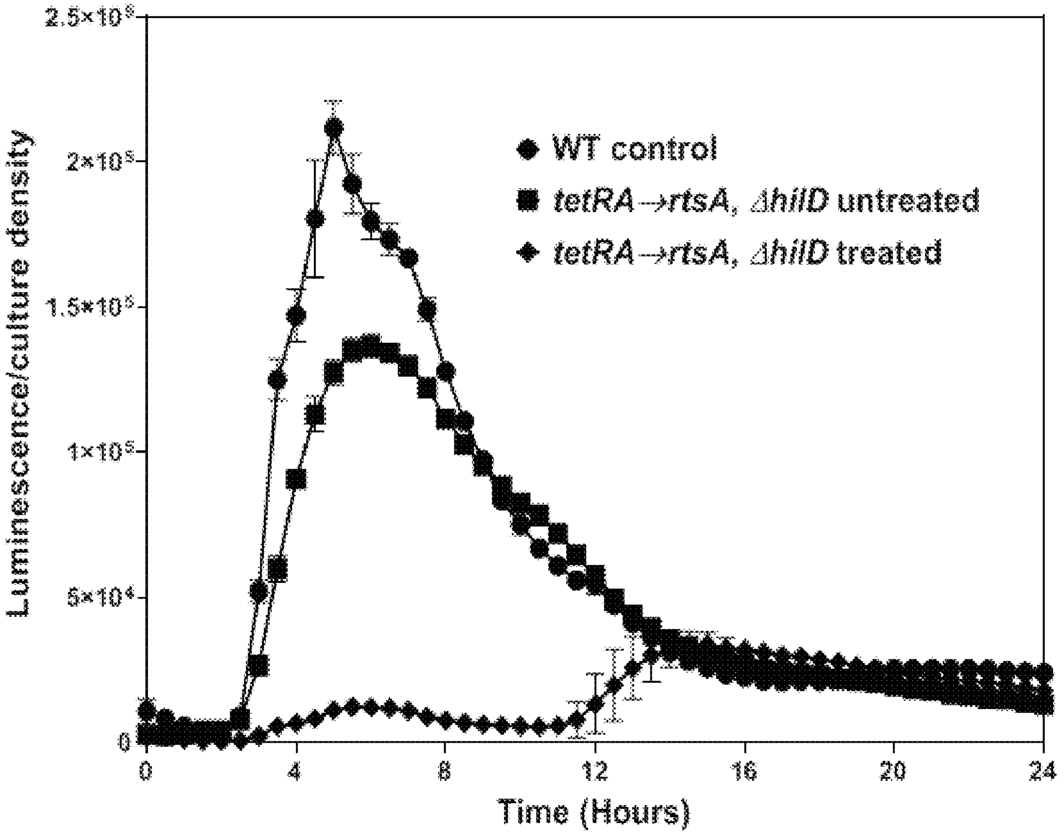
FIGS. 4A-4C. Data showing that the cis-2-hexadecenoic acid DSF primarily targets the central SPI1 regulator HilD post-transcriptionally.
Figure 4B:
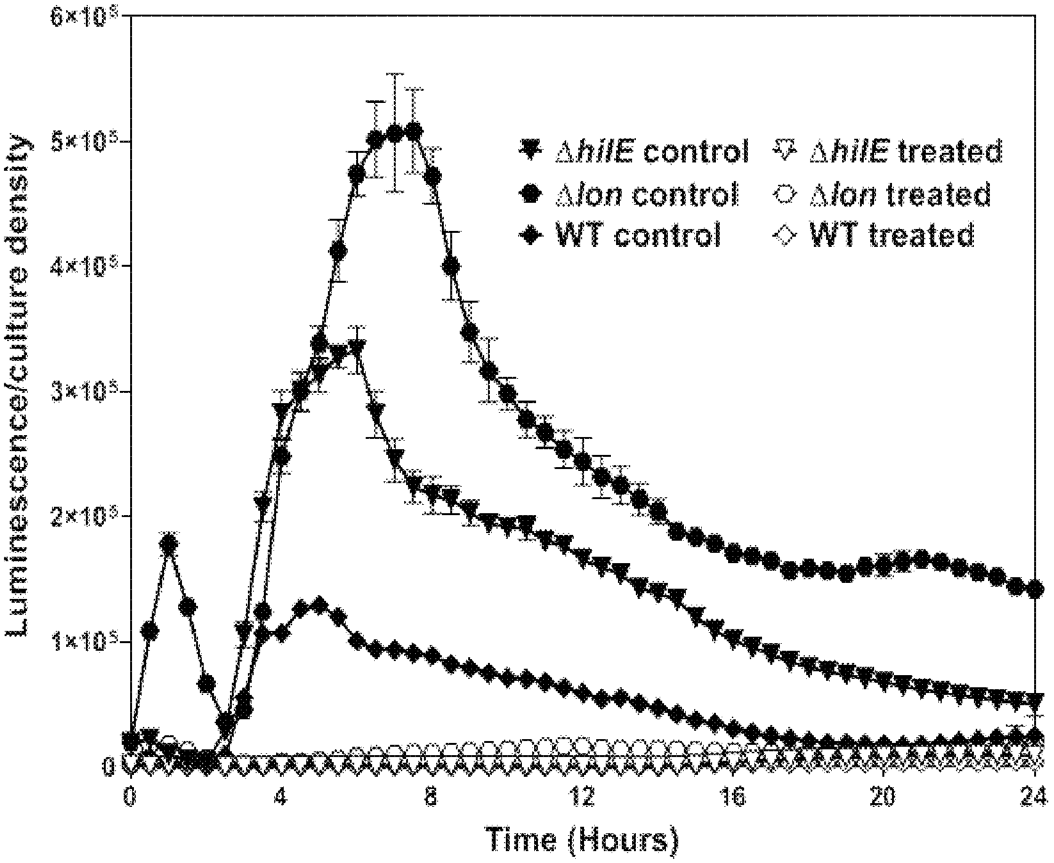

Cis-2-unsaturated fatty acids inhibit the transcription activator of invasion HilD. HilD is known to activate type III secretion complex genes, essential for invasion, both through and independent of hilA (C. D. Ellermeier et al., Ibid.). Short- and long-chain fatty acids have also been shown to repress HilD activity (Y. A. Golubeva et al., Ibid.). To test the importance of HilD in repression by c2-HDA, the present research assessed the expression of sopB in a ΔhilD mutant in the presence of this chemical. In the absence of hilD, the expression of sopB is low, reducing sensitivity of the luciferase assay. As rtsA modestly activates sopB transcription, sensitivity of the assay was improved by increasing expression of rtsA using a regulated tetracycline-inducible promoter (PtetRA) (Y. A. Golubeva et al., *Genetics,* 190(1), 79-90, 2012). c2-HDA repressed sopB by 11-fold, as compared to 68-fold in the wild type, suggesting that most of the repression occurs through HilD, but that other potential means of repression exist (FIG. 4A; FIG. 1C). HilD is under the control of several regulators within and outside of SPI1. It is down-regulated by Lon protease (J. D. Boddicker et al., *Infection and Immunity,* 72(4), 2002-2013, 2004) and HilE (J. R. Grenz et al., *J. Bacteriol.,* 200(8), 2018). As c2-HDA was repressive, the present research tested whether its effects were through these negative regulators. As may be expected, sopB expression was elevated in Δlon and ΔhilE mutants (4- and 3-fold, respectively) compared to a wild type. Despite this increased expression, c2-HDA inhibited sopB expression in these mutants to the level observed in the wild type strain (FIG. 4B). Hence, loss of these regulators had no effect on repression by c2-HDA. These results thus implicate hilD as the target of c2-HDA, but with additional modest effects independent of this regulator.

Figure 4C:
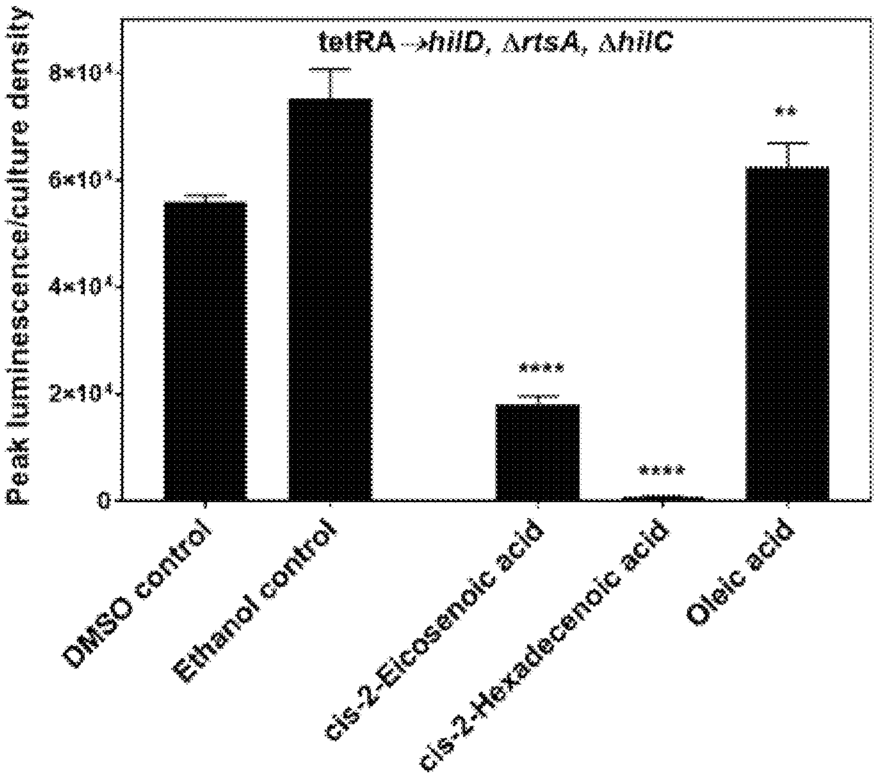

The present research next sought to determine whether these chemicals affect HilD directly and to elucidate the mechanisms of their repression. HilD forms part of a complex feed-forward loop, along with the transcriptional activators RtsA and HilC, which together induce hilA expression (Y. A. Golubeva et al., *Genetics,* 190(1), 79-90, 2012). To isolate the effects of cis-2-unsaturated fatty acids on HilD, hilC and rtsA were deleted, and a hilA::luxCDABE fusion was used to assess invasion gene expression. Additionally, as HilD controls its own transcription, its native promoter was replaced with a tetracycline-inducible promoter. The present research first determined the concentration of tetracycline that induced hilA expression to a level equivalent to that of a wild type (5 μg/ml). Using this level of expression, the present research found c2-HDA repressed hilA by 78-fold, while cis-2-eicosenoic acid and oleic acid repressed less potently, by 3- and 1.2-fold, respectively (FIG. 4C). As the expression of hilD is controlled in this strain, this result thus demonstrates that cis-2-unsaturated fatty acids function to repress invasion gene expression through their post-transcriptional control of HilD.

Figure 5A:
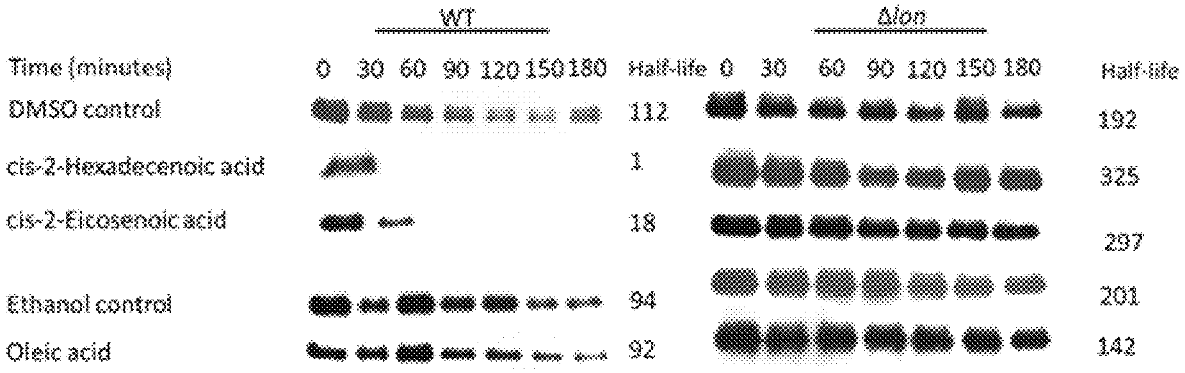
FIGS. 5A-5B. Data showing cis-2-unsaturated fatty acids inactivate HilD with consequent degradation by Lon.
Figure 5B:
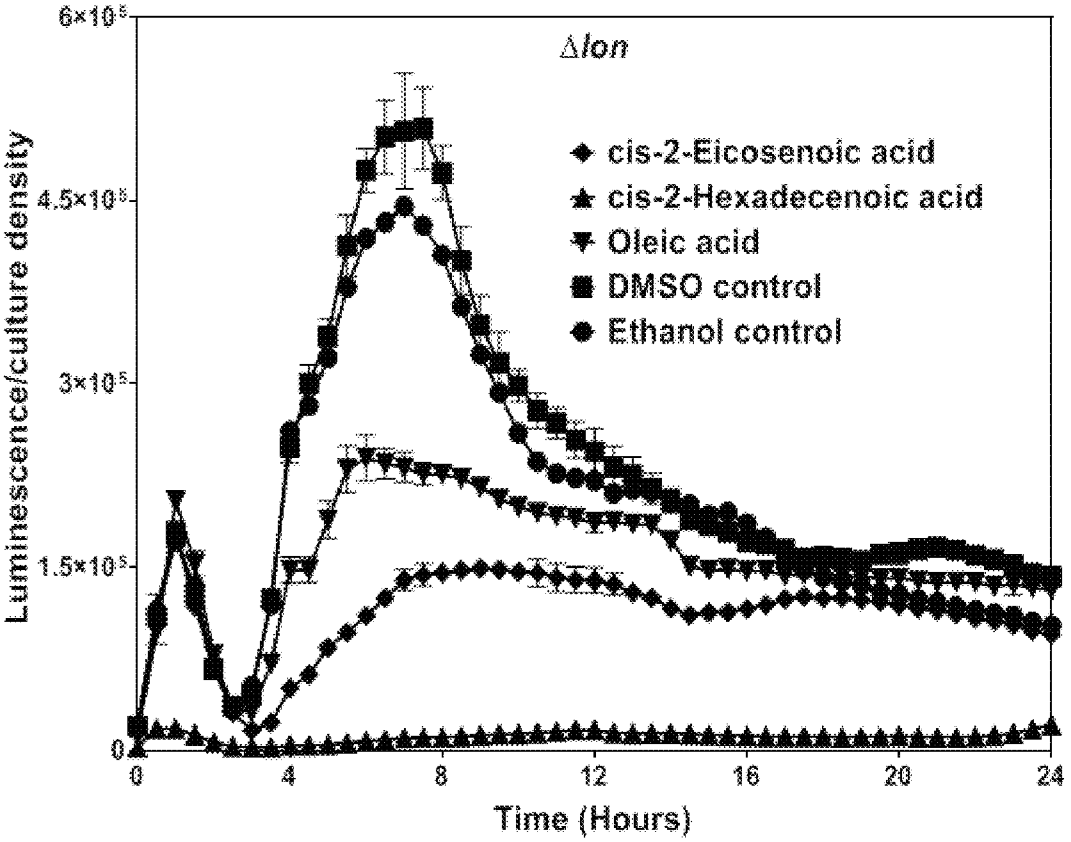

Cis-2-unsaturated fatty acids destabilize HilD. To elucidate the possible mechanisms by which DSFs repressed hilD post-transcriptionally, the present research assessed its effects on HilD protein stability. A strain carrying hilD under a tetracycline-controlled promoter and a C-terminal 3×FLAG tag was used to measure the stability of HilD. The half-life of HilD from bacteria grown in the absence of DSFs was 112 minutes, but the addition of c2-HDA to the culture reduced that half-life drastically, to 1 minute. Consistent with the invasion gene expression results described above, cis-2-eicosenoic acid reduced HilD half-life by a lesser extent, to 18 minutes, and oleic acid did so only slightly (FIG. 5A). The above data indicate that DSFs repress HilD by destabilizing it, as previously reported for short chain fatty acids and bile (C. R. Eade et al., Ibid.). Lon protease is known to be responsible for HilD degradation, but the present genetic approach indicates that Lon was not required for the repressive effects of the c2-HDA (FIG. 4B). The present research therefore tested the role of Lon by assessing HilD protein half-life in a Lon mutant (A. Takaya et al., *Mol. Microbiol.,* 55(3), 839-852, 2005). In the absence of Lon, HilD protein accumulated, and the DSF had no effect on its stability (FIG. 5A). However, the DSF continued to repress hilA expression even in the absence of Lon (FIG. 5B). It is therefore likely that DSFs inactivate HilD with consequent degradation by Lon, but that Lon plays no direct role in the repression of invasion genes by DSFs.

Cis-2-unsaturated fatty acids may target other SPI1 AraC transcriptional regulators. Data presented here show that HilD is important for the repressive effects of c2-HDA on invasion genes. In a hilD mutant, however, c2-HDA continued to demonstrate modest repression of hilA (FIG. 4A), suggesting the existence of additional means, independent of HilD, by which these compounds repress invasion. HilC and RtsA transcriptional regulators bind to the same promoters as does HilD (I. N. Olekhnovich et al., *Journal of Molecular Biology,* 357(2), 373-386, 2006) and the three share a 10% identity in their N-termini (M. T. Gallegos et al., *Microbiol. Mol. Biol. Rev.,* 61(4), 393-410, 1997). Hence, it was reasoned that HilC and RtsA might be additionally targeted by this compound. To test this, the present research utilized strains expressing only one of these regulators, carrying either rtsA or hilC under the control of a tetracycline-inducible promoter, and with null mutations of hilD and the remaining regulator (hilC or rtsA). In the presence of only hilC or rtsA, c2-HDA significantly reduced hilA expression by 20- and 13-fold, respectively, compared to 78-fold in the presence of hilD only (FIGS. 6A and 6B; FIG. 4C). This suggests that c2-HDA may additionally target HilC and RtsA post-transcriptionally, however, with much less pronounced repressive effects compared to HilD.

Figure 7:
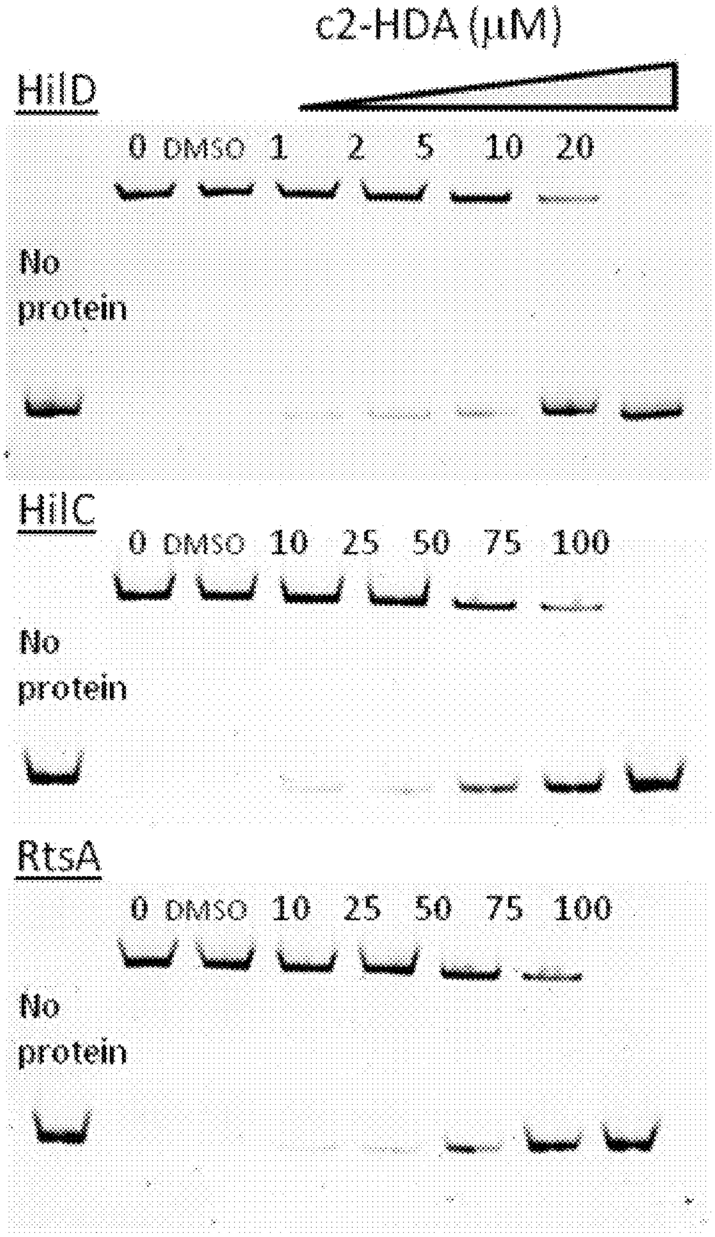
FIG. 7: Data showing that cis-2-hexadecenoic acid inhibits HilD, HilC and RtsA from binding their DNA target. In the presence of 20 μM fatty acid, HilD was completely inhibited from binding hilA promoter DNA, while concentrations of 1, 2, 5 and 10 μM did so partially. For HilC and RtsA, 100 μM cis-2-hexadecenoic acid prevented binding to the hilA promoter, while concentrations of 10, 25, 50 and 75 μM did so partially. All wells contained 10 nM of hilA promoter DNA. The indicated lanes contained 150 μM of protein.

Cis-2-unsaturated fatty acids inhibit HilD, HilC and RtsA from binding their target DNA. The results presented above indicate that cis-2-unsaturated fatty acids repressed HilD through an inactivation mechanism followed by protein degradation. It is hypothesized that these compounds directly interact with HilD, thus impairing its function. HilD binds to the hilA promoter (I. N. Olekhnovich et al., *J. Bacteriol.,* 184(15), 4148-4160, 2002). The present research examined the effects of cis-2-unsaturated compounds on the binding of purified HilD to the hilA promoter using electrophoretic mobility shift assays (EMSA). In the absence of DSF, the expected binding of HilD to the hilA promoter was demonstrated by the retarded migration of this DNA fragment through the polyacrylamide gel (FIG. 7). Addition of 20 μM c2-HDA, however, prevented the binding of HilD to the hilA promoter, whereas concentrations of 1, 2, 5, and 10 μM partially inhibited binding. HilC and RtsA also bind to the hilA promoter and induce expression of hilA. Addition of 100 μM c2-HDA preventing binding of each of these two proteins to the hilA promoter, while concentrations of 10, 25, 50 and 75 μM partially inhibited binding. Therefore, the cis-2-unsaturated fatty acids directly inhibit the ability of HilD, HilC and RtsA to interact with their DNA target.

Figure 8:
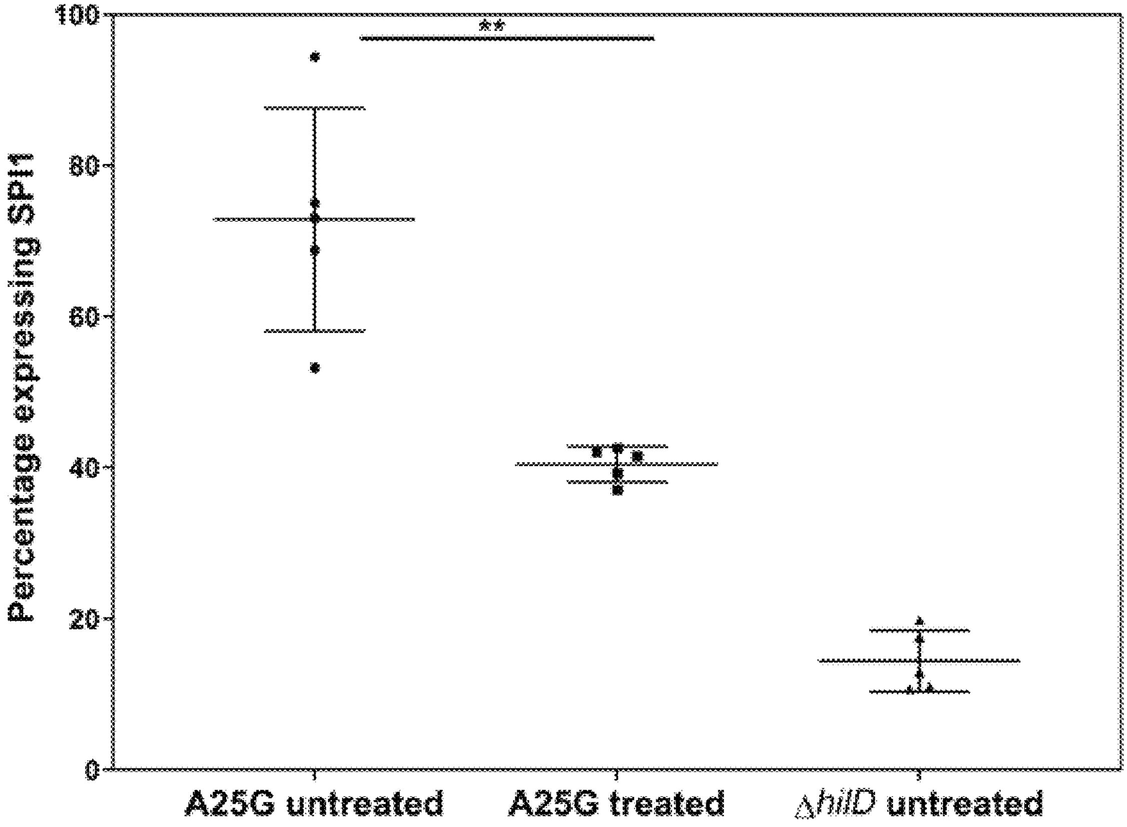
FIG. 8. Data showing that cis-2-hexadecenoic acid reduces the percentage of *Salmonella* expressing SPI in the gut. Three groups of mice (n=5/group) were inoculated with *Salmonella* strains carrying phoN::BFP (for identifying *Salmonella*) and sicA→GFP (for monitoring SPI expression), with either a hilD UTR A25G mutation or a hilD null mutation as shown in the graph. Percentage SPI1 expression was calculated as the portion of BFP-expressing bacteria that also expressed GFP. Data are presented as percentages with means shown by the horizontal lines and the error bars denoting standard deviations. Asterisks denote expression levels significantly different from the control (**-P<0.01).

The DSF c2-HDA represses invasion-gene expression in a mouse colitis model. Data presented above show that DSFs potently repress HilD, and also repress HilC and RtsA. The present research next tested whether this signal would inhibit SPI1-encoded invasion-gene expression in the complex chemical environment of the gut. Only a portion of bacteria activate invasion genes in the gut (M. Diard et al., *Nature,* 494(7437), 353-356, 2013). To improve the sensitivity of the assay, the present research used a strain carrying a hilD UTR A25 to a G single base mutation, resulting in increased invasion-gene expression due to altered mRNA stability (C. C. Hung et al., *Plos Pathogens,* 15(4), 2019). This strain additionally carried a constitutively expressed ΔphoN::BFP construct for *Salmonella* identification, and a sicA-GFP reporter fusion to monitor SPI1 expression. The administration of c2-HDA to mice at 1.5 mM in drinking water significantly reduced the percentage of bacteria expressing SPI1 in the caecum by 2-fold. The proportion of a ΔhilD null mutant expressing SPI1 was 5-fold lower than the untreated A25G strain, indicating the importance of HilD for invasion activation in the gut (FIG. 8). As fatty acids are rapidly absorbed in the upper gastrointestinal tract, it was presumed that low amounts of c2-HDA were available in the caecum. Compared to the in vitro potency of c2-HDA, an estimated concentration of between 2.5 μM and 10 μM would repress SPI1 to the percentage observed in the caecum. Overall, these results demonstrate that the DSF c2-HDA can signal to inhibit invasion gene expression in the gut.

Discussion

The above data shows that cis-2-unsaturated fatty acids, employed as quorum-sensing signals by a range of bacterial species, potently regulate virulence genes in enteric pathogens. In *Salmonella,* c2-HDA interacts with the central SPI1 transcriptional regulators HilD, HilC and RtsA, members of the AraC family, preventing them from binding their DNA target (FIG. 7). The transcriptional regulators of this family are well known for effector-mediated transcriptional control of metabolic pathways (M. T. Gallegos et al., Ibid.). Accumulating evidence that AraC-type transcriptional regulators control virulence has elicited investigation into the environmental signals that they sense (B. H. Abuaita et al., Ibid.).

Figure 6A:
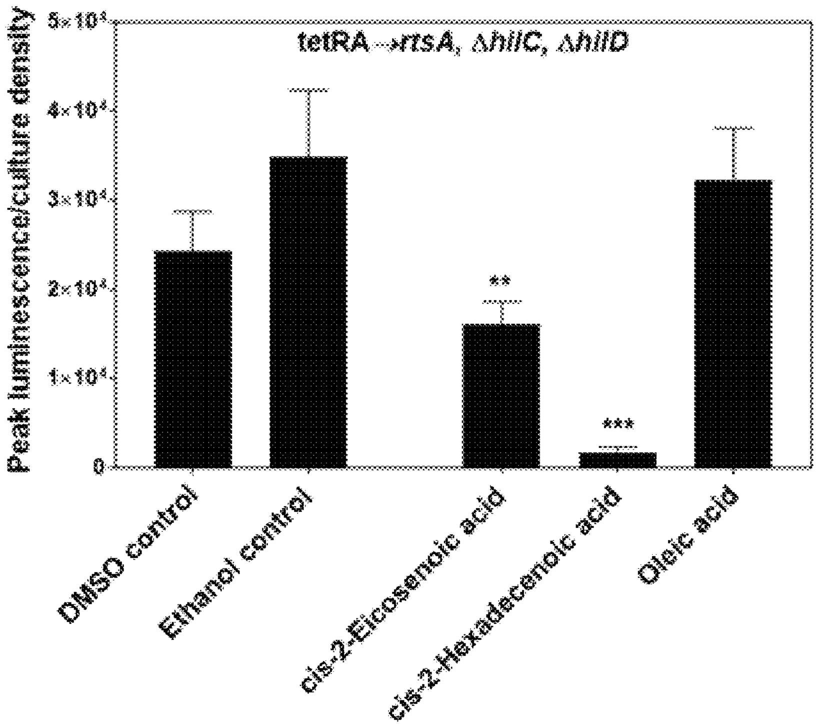
FIGS. 6A-6B. Data showing that cis-2-unsaturated fatty acids may additionally repress other SPI1 transcriptional regulators of the AraC family. Strains carrying a hilA::lux reporter fusion, with either rtsA or hilC under the control of a tetracycline-inducible promoter, and with null mutations of hilD and the remaining regulator (rtsA or hilC), were used.
Figure 6B:
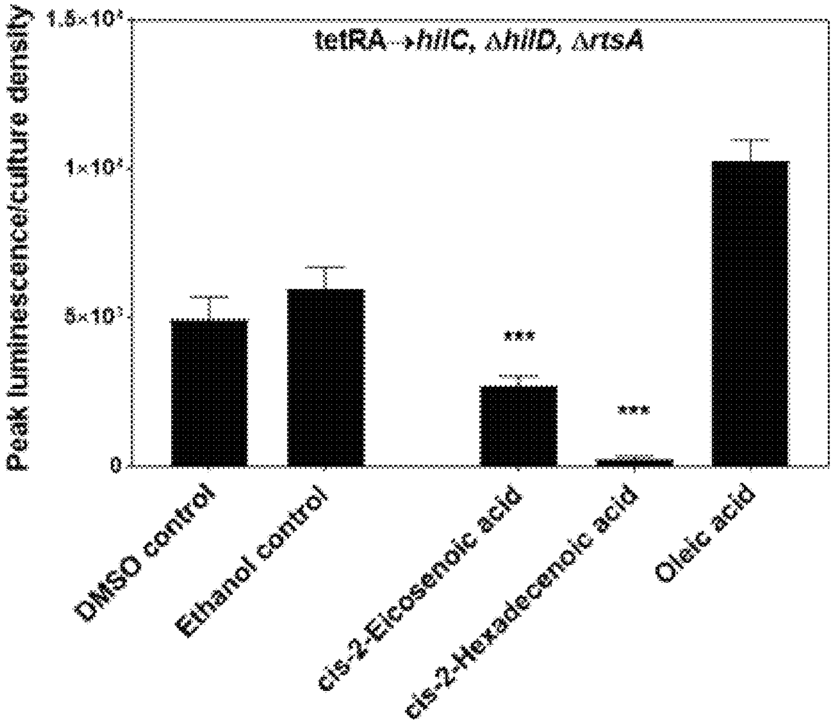

In *Salmonella* and other important enteric pathogens, AraC-type transcriptional regulators of pathogenicity elements have been reported to sense long-chain fatty acids (M. J. Lowden, *PNAS USA,* 107(7), 2860-2865, 2010). The animal host secretes bile, containing a mixture of unsaturated fatty acids and surfactants, into the gut lumen for digestion of lipids and protection from pathogens (J. L. Boyer, *Compr. Physiol.,* 3(3), 1035-1078, 2013). Enteric pathogens, however, have adapted to resist killing by bile and further have integrated bile as a signal of their entry into a host (J. S. Gunn, *Microbes and Infection,* 2(8), 907-913, 2000). Similarly, they likely use fatty acids as cues for the activation of virulence at the appropriate niche of the gut (C. C. Hung et al., Ibid.). cis-2-unsaturated fatty acids function as quorum sensing signals in Proteobacteria, including pathogens of plants and animals, where they signal by regulating c-di-GMP turnover, leading to the regulation of virulence factors (C. E. Barber et al., Ibid.). In *Salmonella,* however, the data presented herein has demonstrated a novel mechanism: the fatty acids interact with the AraC-type transcriptional regulators HilD, HilC and RtsA to control a cascade of invasion genes (FIG. 4C; FIGS. 6A and 6B; FIG. 7).

The data indicates that c2-HDA binds HilD directly as has been shown for other fatty acids with ToxT (M. J. Lowden et al., Ibid.). Deactivated HilD is consequently degraded by Lon, reducing the half-life of HilD dramatically. The ability of specific cis-2-unsaturated fatty acids to potently repress HilD raises the question of whether HilD naturally interacts with this class of chemicals in the gut. It is unknown whether *Salmonella* encounters DSFs within an animal host, but it is clear that bacterial species present in the gut are capable of DSF production. Metagenomic analyses have reported the existence of the DSF-producing genus *Burkholderia* in wild and laboratory mice (J. Shin et al., *Scientific Reports,* 6, 2016). *Stenotrophomonas maltophilia*, which contains a DSF quorum-sensing system related to that of *Xanthomonas* (S. Q. An et al., *BMC Res. Notes,* 11(1), 569, 2018), is a constituent of the crypt-specific core microbiota of the murine colon, where it is thought to play an important role in crypt protection (T. Pedron et al., *MBio,* 3(3), 2012). However, the DSFs of *Burkholderia* and *Stenotrophomonas*, cis-2-dodecenoic acid and cis-11-methyl-2-dodecenoic acid, respectively, are less potent in repressing invasion genes than c2-HDA. DSF signaling between species and even kingdoms, resulting in the control of behaviors like biofilm formation, has been reported (C. Boon et al., Ibid.). Due to the great sensitivity of *Salmonella* to highly specific members of the DSF class, it is herein surmised that this enteric pathogen senses interspecies signals as a cue to its location within the gut and consequently modulates the expression of its virulence determinants.

With the widespread and growing occurrence of antibiotic resistance, remedies aimed at attenuating virulence rather than survival of pathogens would help alleviate selection pressure, and thus, DSFs provide such an opportunity to be explored for the control of *Salmonella* disease and colonization. c2-HDA, in particular, is capable of inhibiting SPI1-encoded invasion-gene expression at very low concentration and may thus function as an inhibitor of *Salmonella* infection (FIG. 1A). Furthermore, the inactivation of HilD by c2-HDA leading to its rapid degradation is an elegant mechanism for the irreversible deactivation of invasion. In the gut, despite the rapid absorption, it is likely that a low micromolar range of c2-HDA is sufficient to repress invasion-gene expression (FIG. 8). It may be predicted that HilD mutants, resistant to the action of c2-HDA, would arise. However, c2-HDA likely represses the three SPI1 alternate AraC transcriptional regulators, HilC and RtsA in addition to HilD (FIG. 4; FIG. 6; FIG. 7), and thus, the probability of simultaneous mutations occurring is remote.

While there have been shown and described what are at present considered the preferred embodiments of the invention, those skilled in the art may make various changes and modifications which remain within the scope of the invention defined by the appended claims.

What is claimed is:

1. A method for treating *Salmonella* infection in a subject in need thereof, the method comprising enterally administering to said subject a pharmaceutical composition containing a pharmaceutically effective amount of a fatty acid dissolved or suspended in a pharmaceutically acceptable carrier, wherein said pharmaceutical composition excludes an additional antibiotic, and said fatty acid has the following structure:

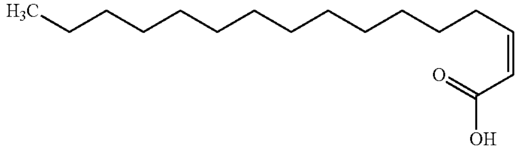

cis-2-Hexadecenoic acid and wherein the pharmaceutically effective amount of the fatty acid is present in a concentration of 100 nM to 20 mM in said pharmaceutically acceptable carrier.

2. The method of claim 1, wherein said pharmaceutically acceptable carrier comprises a liquid selected from an alcohol, glycol, oil, or dimethyl sulfoxide.

3. The method of claim 1, wherein said fatty acid is administered orally.

4. The method of claim 3, wherein said fatty acid is within a capsule when administered orally.

5. The method of claim 1, wherein said subject is human.

6. The method of claim 1, wherein said subject is an animal.

7. The method of claim 1, wherein said fatty acid is administered in a dosage of 50 mg to 2000 mg daily for at least one day.

8. The method of claim 1, wherein *Salmonella* infection is inhibited in said subject.

9. The method of claim 1, wherein *Salmonella* infection is prevented in said subject.

10. The method of claim 1, wherein said fatty acid inhibits expression of at least one *Salmonella* invasion gene.

* * * * *